(12) United States Patent
Fisker et al.

(10) Patent No.: US 8,974,229 B2
(45) Date of Patent: Mar. 10, 2015

(54) VIRTUALLY DESIGNING A POST AND CORE RESTORATION USING A DIGITAL 3D SHAPE

(71) Applicant: 3Shape A/S, Copenhagen K (DK)

(72) Inventors: Rune Fisker, Virum (DK); Sven Nonboe, Hillerød (DK)

(73) Assignee: 3Shape A/S, Copenhagen K (DK)

( * ) Notice: Subject to any disclaimer, the term of this patent is extended or adjusted under 35 U.S.C. 154(b) by 0 days.

(21) Appl. No.: 13/761,377

(22) Filed: Feb. 7, 2013

(65) Prior Publication Data

US 2013/0209965 A1 Aug. 15, 2013

Related U.S. Application Data

(60) Provisional application No. 61/597,395, filed on Feb. 10, 2012.

(30) Foreign Application Priority Data

Feb. 10, 2012 (DK) .................................. 2012 00107
Oct. 19, 2012 (DK) .................................. 2012 70640

(51) Int. Cl.
*A61C 13/30* (2006.01)
*A61C 13/00* (2006.01)
(Continued)

(52) U.S. Cl.
CPC ............... *A61C 13/0004* (2013.01); *A61C 5/08* (2013.01); *A61C 9/0046* (2013.01); *A61C 13/30* (2013.01)
USPC .......................................... 433/224; 433/220

(58) Field of Classification Search
USPC ...................... 433/72, 74, 215, 224, 225, 220
See application file for complete search history.

(56) References Cited

U.S. PATENT DOCUMENTS 5,538,424 A * 7/1996 Gelb ................................ 433/72
5,690,490 A * 11/1997 Cannon et al. ................. 433/141
(Continued)

FOREIGN PATENT DOCUMENTS

CN 101803958 A 8/2010
EP 0 904 743 A2 3/1999
(Continued)

OTHER PUBLICATIONS

Extended European Search Report issued on Oct. 4, 2013, by European Patent Office in corresponding European Patent Application No. 13154219.3 (7 pages).
(Continued)

*Primary Examiner* — Ralph Lewis
(74) *Attorney, Agent, or Firm* — Buchanan Ingersoll & Rooney PC

(57) ABSTRACT

A method of virtually designing a post and core restoration for attachment in a damaged tooth of a patient, where the tooth includes a bore for receiving the post of the post and core, the method includes obtaining a first 3D scan includes at least a part of the damaged tooth; providing a digital 3D shape adapted to fit the bore of the damaged tooth; virtually matching the first 3D scan of the tooth and the digital 3D shape, where the matching includes matching a surface region in the first 3D scan of the tooth with a corresponding surface region of the digital 3D shape, such that at least part digital 3D shape is represented relative to the first 3D scan of the tooth; and virtually designing the post and core restoration based on the representation of the digital 3D shape relative to the first 3D scan of the tooth.

16 Claims, 27 Drawing Sheets

(51) Int. Cl.
*A61C 5/08* (2006.01)
*A61C 9/00* (2006.01)

(56) References Cited

U.S. PATENT DOCUMENTS

| | | | |
|---|---|---|---|
| 6,882,894 B2 * | 4/2005 | Durbin et al. | 700/118 |
| 2006/0228676 A1 * | 10/2006 | Brown et al. | 433/220 |
| 2007/0141536 A1 | 6/2007 | Provost et al. | |
| 2011/0136080 A1 | 6/2011 | Holzner et al. | |
| 2012/0065943 A1 * | 3/2012 | Fisker et al. | 703/1 |

FOREIGN PATENT DOCUMENTS

| | | | |
|---|---|---|---|
| WO | WO 2010/09709 | * | 9/2010 |
| WO | WO 2010/097089 A1 | | 9/2010 |

OTHER PUBLICATIONS

Danish Search Report dated Sep. 20, 2012, issued in corresponding Danish Patent Application No. PA 2012 00107. (2 pages).

* cited by examiner

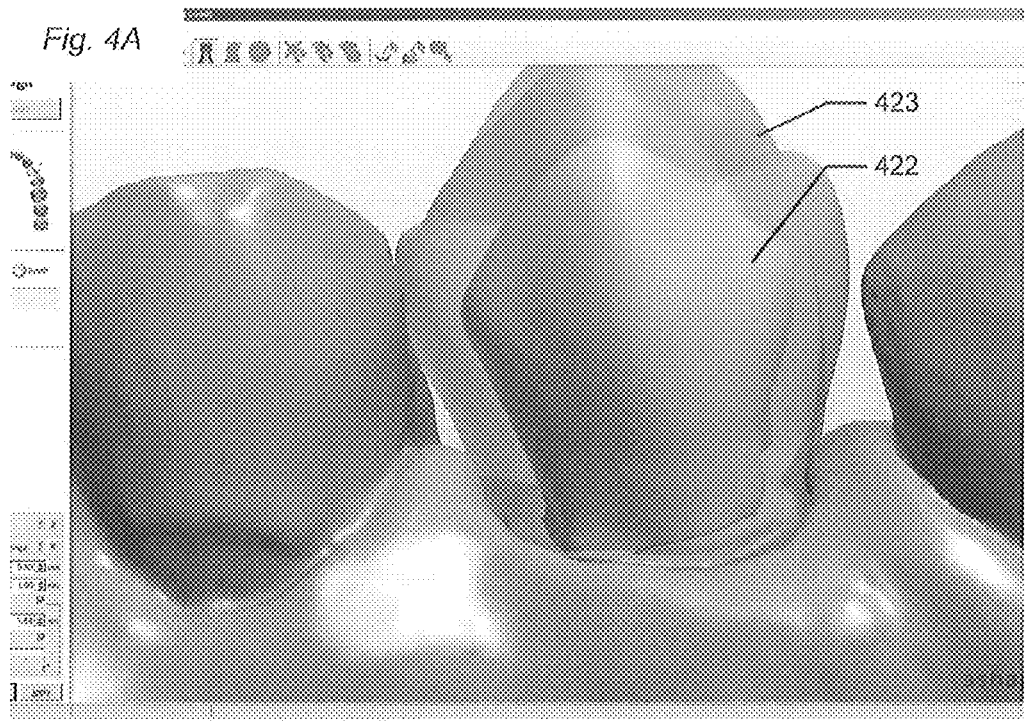
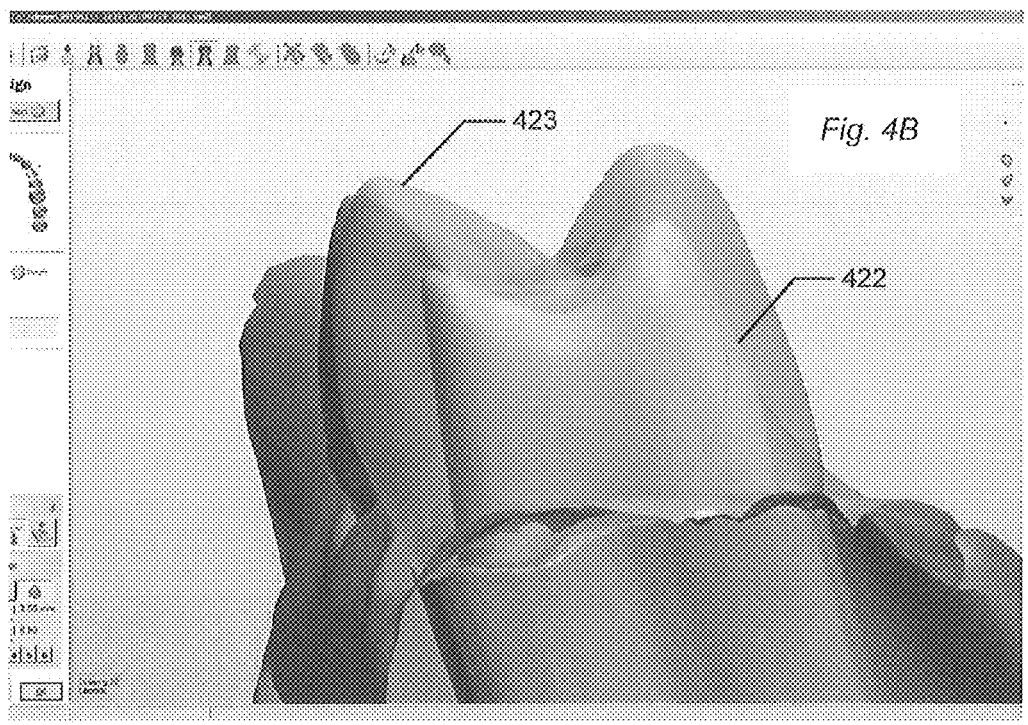

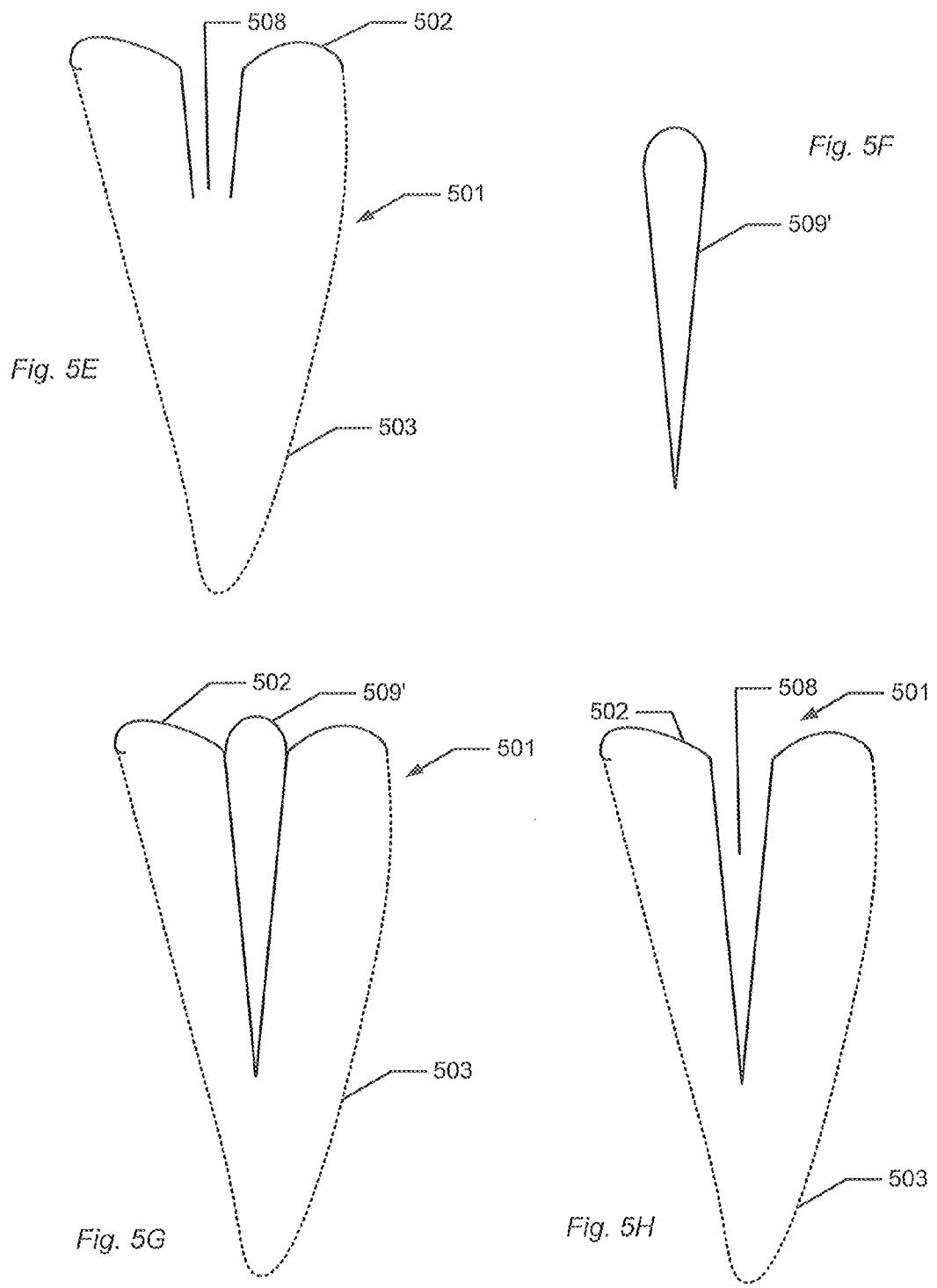

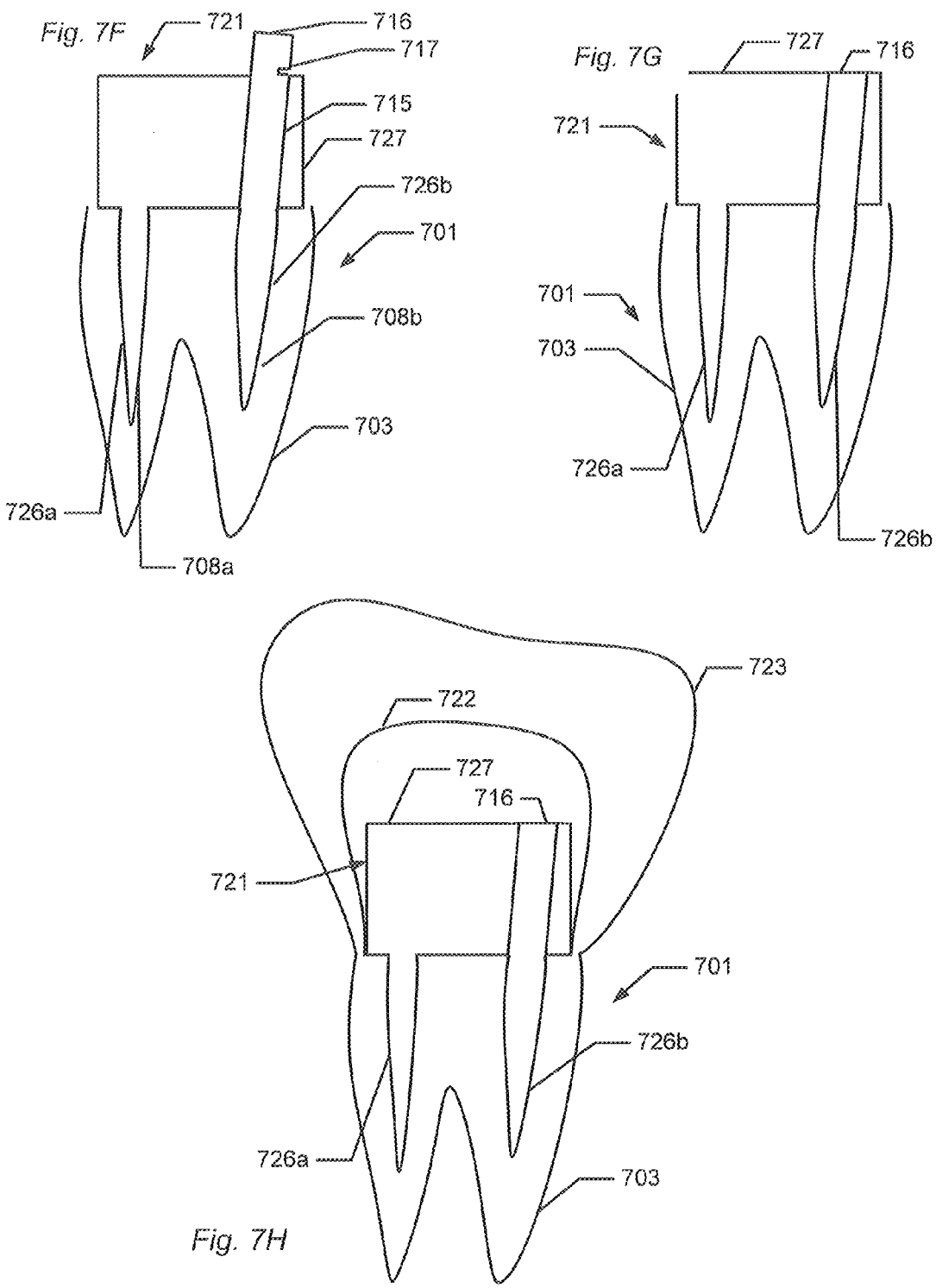

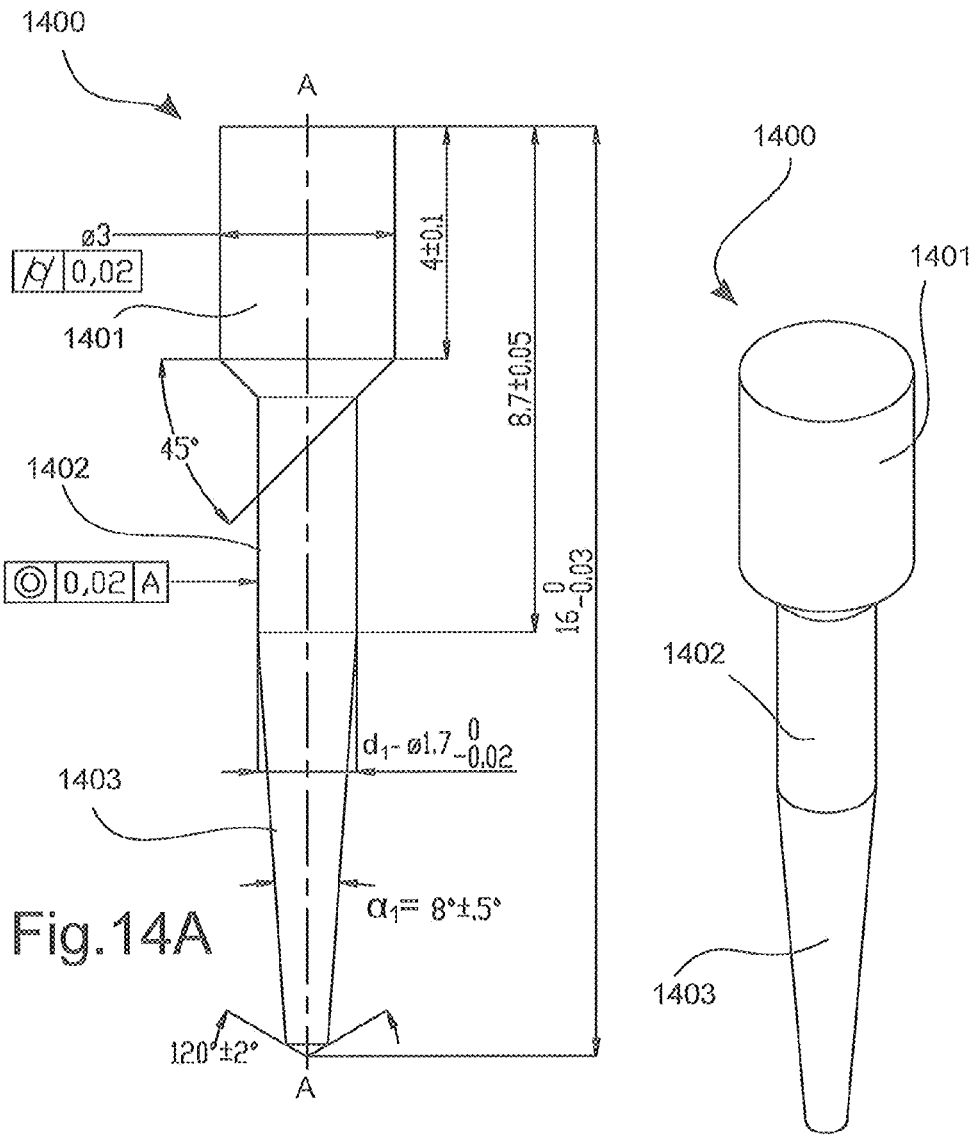
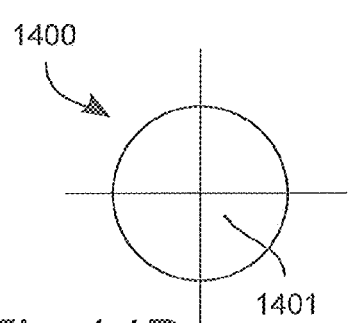
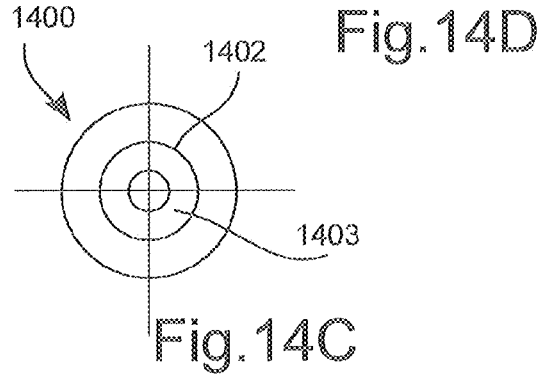

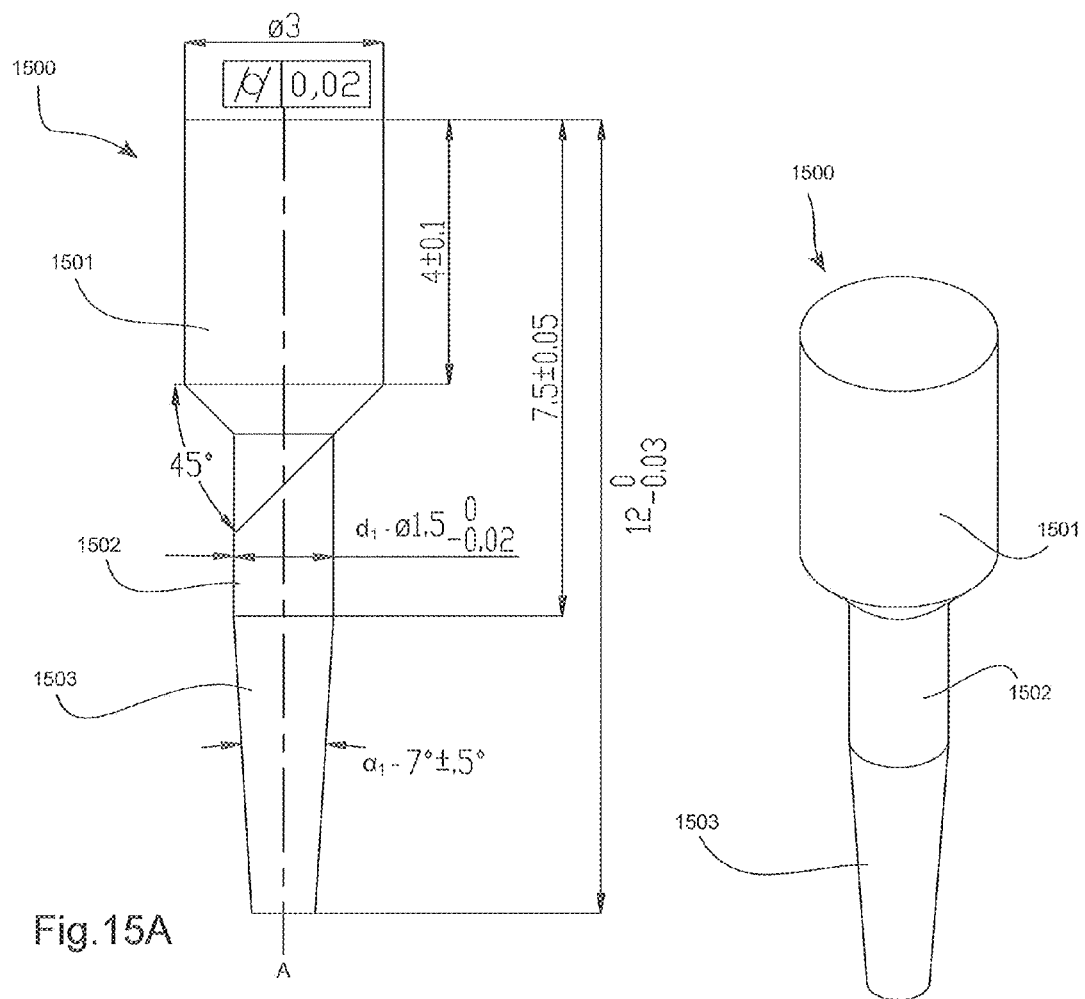
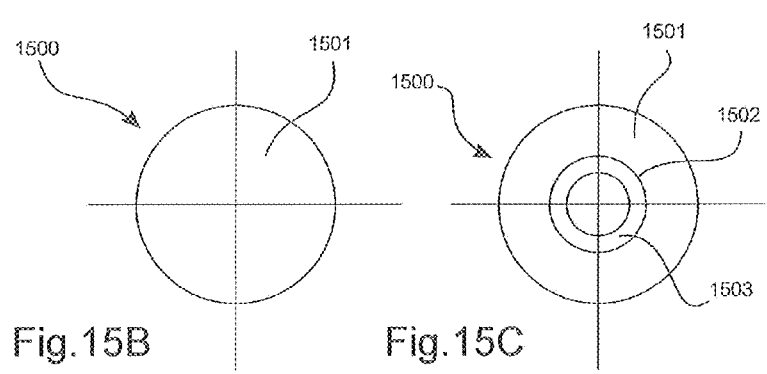
Fig.15A
Fig.15B  Fig.15C  Fig.15D

VIRTUALLY DESIGNING A POST AND CORE RESTORATION USING A DIGITAL 3D SHAPE

FIELD OF THE INVENTION

This invention generally relates to a system and a method for virtually designing a post and core restoration adapted for attachment in a damaged tooth of a patient.

BACKGROUND OF THE INVENTION

A post and core is a dental restoration used to sufficiently build-up tooth structure for future restoration with a crown when there is not enough tooth structure to properly retain the crown due to loss of tooth structure to either decay or fracture. In many cases the dental root is removed leaving an empty root canal in the tooth. Typically a thin rigid post (e.g. metal post) is inserted into the root canal and this post provides retention for a "core" which is a build up of material that replaces the lost tooth structure. The post can be cemented within the root canal and the core, which is an artificial preparation provides retention for the crown or coping replacing the tooth. The term "post and core" is also referred to as "post-and-core" and "inlay core". Post and core restorations are often characterized as "foundation restorations".

In a root canal procedure the nerve of the tooth is typically removed by the dentist using a dental drill, a so called endodontic procedure, leaving a bore in the tooth. In many cases a special post can be provided that matches the shape of the drill and after drilling the post can be directly cemented in the bore. However, the tooth root canal may have a non-regular structure and the bore in the tooth after removing the root is often also irregular, but even for the regular shapes the depth of the bore may be unknown. No post can thereby match the bore and a custom post must be provided.

A typical procedure when designing a post and core is that the dentist provides an impression of the prepared tooth with the bore and possibly also adjacent teeth and sends it typically to a dental technician at a dental laboratory. From this impression a dental model, such as a gypsum model, can be poured, and the dental restoration including the post and core can now be build from the dental model. The dental technician typically builds the post and core in wax, and then performs an investment casting, such that the real post and core is manufactured in a suitable material, e.g. a metal alloy.

WO10097089A discloses a computer-implemented method of designing and/or manufacturing a post and core to match a bore of a tooth, said method comprising the steps of: a) obtaining at least one impression of a set of teeth comprising a bore; b) scanning the impression of the set of teeth comprising the bore; c) providing a three-dimensional scan representation of the impression comprising the bore; d) transforming the three-dimensional scan representation to a three-dimensional positive working model of the set of teeth and the bore; and e) designing a post and core model from the positive working model of the bore.

Furthermore it is disclosed that when removing the tooth root/tooth nerve the dentist have used one or more dental drills. Thus, the shape of the resulting tooth bore is at least partly determined by the shape and/or type of the drill(s) processing the bore. In a further embodiment of the invention the post and core model and/or the post model is matched with the shape of the dental drill that created the bore. This is provided to improve the post and core model. Matching the shape can be merging and/or combining shape information of the dental drill(s) that created the bore, shape information such as a CAD model of the drill(s). Thereby scan artefacts of the post and core model can be identified and/or removed. E.g. a notch or cut in the post and core model can be identified as a scan artefact by knowing that use of the particular drill used could not have provided such a notch or cut.

It remains a problem to provide an alternative method for virtually designing a post and core restoration.

SUMMARY

Disclosed is a method of virtually designing a post and core restoration adapted for attachment in a damaged tooth of a patient, where the damaged tooth comprises a bore for receiving the post of the post and core, wherein the method comprises:

obtaining a 3D image comprising a first 3D scan comprising at least a part of the damaged tooth;

providing a digital 3D shape adapted to fit the bore of the damaged tooth;

virtually matching the first 3D scan of the tooth and the digital 3D shape, where the matching comprises matching a surface region in the first 3D scan of the tooth with a corresponding surface region of the digital 3D shape, such that at least part digital 3D shape is represented relative to the first 3D scan of the tooth;

virtually designing the post and core restoration based on the representation of the digital 3D shape relative to the first 3D scan of the tooth.

This advantageously provides a method where a complete representation of the damaged tooth and in particularly the bore thereof may be provided. This solves the problem of facilitating the design of a post and core restoration.

In one embodiment the digital 3D shape is at least a part of a surface representation adapted for matching at least a part of the bore of the damaged tooth.

This is for example advantageous when the digital 3D shape is a scan of an impression of the damaged tooth including the bore where a part of the impression matches the bore shape. Dental impressions, i.e. negatives of the teeth, are difficult to scan as the teeth create deep recesses which are difficult to scan into. Alternatively a first 3D scan may be taken of the teeth by using an intra oral scanner or by scanning a gypsum model. The digital 3D shape is obtained by scanning a small impression of the damaged tooth taken by the dentist directly in the mouth or by a dental technician on the gypsum model. A small impression of the damaged tooth will be easy to scan since the negative shape of the bore will create a shape without significant cavities where the scanner easily may detect the surfaces.

Accordingly, by combining the first 3D scan and the digital 3D shape provided via a scan of the impression of the damaged tooth a highly detailed representation of a set of teeth and the damaged tooth for designing the post and core can be provided.

In another embodiment the method comprises that the digital 3D shape is at least a part of a component adapted for fitting to the damaged tooth, where the component comprises at least a post part adapted for fitting in the bore of the damaged tooth. This will be discussed in further detailed below.

Additionally, the description also related to a combination of a first 3D scan such as a general scan of the teeth, a first digital 3D shape such as a scan of an impression of the damaged tooth where the first digital 3D shape matches the bore, and a second digital 3D shape such as a component where the second digital 3D shape fit in the bore.

It should be understood that the term "fit" is used as a generic term covering "matching" and "fit in". Accordingly, a digital 3D shape which "matches" the bore will have a shape that represents the actual bore shape. However, a digital 3D shape which "fit in" the bore will have a shape which allows a component manufactured therefrom to be placed in the bore.

Moreover, it should be understood that the 3D image may comprise several different scans, such as the first 3D scan and a second 3D scan as will be discussed. It may also comprise further scans or other 3D models obtained by other means than scanning. The 3D image may for example comprise an identification tag which allows the user to easily identify that he or she is working with the correct 3D image.

Disclosed is a method of virtually designing a post and core restoration adapted for attachment in a damaged tooth of a patient, where the damaged tooth comprises a bore for receiving the post of the post and core, wherein the method comprises:

- obtaining a 3D image comprising a first 3D scan comprising at least a part of the damaged tooth;
- providing a digital 3D shape of at least a part of a component adapted for fitting to the damaged tooth, where the component comprises at least a post part adapted for fitting in the bore of the damaged tooth;
- virtually matching the first 3D scan of the tooth and the digital 3D shape of the component, where the matching comprises matching a surface region in the first 3D scan of the tooth with a corresponding surface region of the digital 3D shape component, such that at least part of the post part of the digital 3D shape of the component is represented relative to the first 3D scan of the tooth;
- virtually designing the post and core restoration based on the representation of the post part of the digital 3D shape of the component relative to the first 3D scan of the tooth.

The first 3D scan may be denoted the 3D scan in the following.

The method comprises that the 3D scan can be an intra oral scan or a model scan of the damaged tooth, where the component may be the post of the post of the post and core, as the post of the post and core is adapted for fitting and being arranged in the tooth when the post and core is finally attached or cemented in the damaged tooth. The 3D scan may be performed such that at least part of the bore or cavity of the tooth is obtained. The matching is performed by means of matching the bore, i.e. the obtained part of the bore, of the tooth from the 3D scan with the digital 3D shape of the post.

The 3D digital shape of the post may be known, because the it may be the same shape as the drill which was used to drill the bore in the tooth.

The method also comprises that the 3D scan can be an impression scan, where the component may be a scan pin arranged in the damaged tooth during the scanning, and where the scan pin comprises an inner part corresponding to the post of the post and core, where the matching is performed by means of matching the inner part of the scan pin from the 3D scan with the digital 3D shape of the inner part of the scan pin, since the inner part of the scan pin is the part which is scanned in an impression scan.

The method also comprises that the 3D scan can be an intra oral scan or a model scan, where the component may be a scan pin arranged in the damaged tooth during the scanning, and where the scan pin comprises an outer part and an inner part corresponding to the post of the post and core, where the matching is performed by means of matching the outer part of the scan pin from the 3D scan with the digital 3D shape of the outer part of the scan pin, since the outer part of the scan pin is the part which is scanned in an intra oral scan and in a model scan.

It is an advantage that by determining the arrangement, position and/or orientation of the post part of the digital 3D shape, e.g. a CAD file, relative to the 3D scan of the tooth, the post and core can be designed so that the post fits in the bore in the tooth, and the core fits on the post and to the tooth stump and to the neighbor teeth. Thus it is an advantage that the method may comprise:

- virtually applying and/or providing the post part from the digital 3D shape to the 3D scan of the tooth based on the virtual matching;
- determining the arrangement and/or position and/or orientation of the post part relative to the tooth in the 3D scan;
- obtaining the true surface of the post part from the digital 3D shape of the component.

The arrangement of the post relative to the tooth may comprise the position and/or orientation of the post.

Determining the arrangement of the post part may comprise visualizing, obtaining and/or providing the post.

The arrangement of the post part relative to the tooth may comprise determining and/or deriving and/or visualizing and/or identifying etc. the size, direction, position, orientation etc. of the post part relative to the tooth, such that the post and core can be designed based on the post part, where the post part is corresponding to the post or the post and core.

Since the at least part of the post part of the digital 3D shape of the component is represented relative to the first 3D scan of the tooth, this can be used to design the post and core, since when knowing the exact position, orientation, depth etc that the post should have in the tooth for providing a good retention, the final post and the final core fitting to the post and to the remainder of the tooth structure can be designed to obtain a perfectly fitting post and core with good retention and strength.

It is an advantage that the post part can be determined relative to the tooth, since a post and core need not be rotation symmetric as an implant, so it may be even more important for the attachment, functionality and/or aesthetics that the core is correctly arranged relative to the post.

The following rules may apply when designing a post and core restoration: For optimal post preparation:

- use a length equal to or greater than the length of the final crown;
- maintain a minimum of 4 mm apical-gutta-percha seal.
- Shorter posts are undesirable because they:
- are less retentive;
- produce unfavorable stresses within the root;
- predispose to fracture;
- result in loss of cementation It is an advantage of the method that the 3D shape of the bore may be derived based on the matching of the 3D scan of the tooth and the digital 3D shape of the component, and that the post and core restoration may be virtually designed based on the derived 3D shape of the bore.

Thus the 3D scan of the tooth and the digital 3D shape may be represented or visualized together.

It is an advantage that the 3D digital shape of the post part is used to or is basis for designing, deriving, representing, reconstructing, and/or constructing at least part of the bore.

Thus it is an advantage that the exact shape of the post and/or bore is reconstructed based on the matching.

The attachment of the manufactured post and core restoration in the damaged tooth may be by means of cementation, gluing, chemical bonding etc.

The post of the post and core may fit exactly in the bore, since the post may be identical to, similar to, equivalent to, and/or corresponding to the drill used by the dentist to drill the bore in the damaged tooth.

The post of the post and core may be placed at least partly in the bore or root canal of the tooth.

The tooth may have more root canals, and a bore may have been drilled in one or more of the root canals, and there may thus be a post in one or more of the root canals. Thus the post and core may comprise more posts, also denoted a post and core with multiple posts.

For virtually designing a post and core with multiple posts, a scan pin may be inserted in each bore at a time, and the scan pin may then be scanned in each bore. All the scans of the scan pin in each bore may be used together to design the post and core with multiple posts.

The digital 3D shape of the component may be a CAD file of the component providing 3D information on the shape of the component.

The 3D scan may be a surface scan obtaining the surface of the scanned tooth.

Matching the 3D scan of the tooth with the digital 3D shape of the component may be denoted as aligning, overlaying, combining, fitting etc.

The 3D scan may be denoted a 3D representation.

The scan pin may be denoted a scan body. The outer part of the scan pin may be denoted the visible part or flag part. The inner part of the scan pin may be denoted the invisible part or the base part. Visible and invisible is for the scanner scanning the tooth, since the outer part is at least partly present outside the tooth and thereby visible when performing a surface scan, whereas the inner part is adapted to be present in the bore/root canal inside the tooth and thereby not visible when performing a surface scan.

The scan pin may have any suitable shape and size. The inner part may typically be up to 1 cm long, such as about 1 mm, 2 mm, 3 mm, 4 mm, 5 mm, 6 mm, 7 mm, 8 mm, 9 mm or 10 mm. If the root of the tooth and/or the root canal or bore is very long, the scan pin may of course be longer. The outer part of the scan pin may typically be rectangular, such as quadratic, oblong etc. The sides of the outer part may typically be about 4 mm or 5 mm, such as about 1 mm, 2 mm, 3 mm, 6 mm, 7 mm, 8 mm, 9 mm or 10 mm.

Scanning Teeth without Use of Scan Pin

In some embodiments the digital 3D shape of the component is a digital 3D shape of a post corresponding to the post of the post and core.

Thus the digital 3D shape of the component may comprise only a post or a post part, i.e. the component is a post, and the digital 3D shape of the component is a post.

According to an aspect of the invention disclosed is a method of virtually designing a post and core restoration adapted for attachment in a damaged tooth of a patient, wherein the method comprises:
  obtaining a 3D image comprising a first 3D scan comprising at least part of the damaged tooth;
  providing a digital 3D shape of a post corresponding to the post of the post and core;
  virtually matching the first 3D scan of the tooth and the digital 3D shape of the post, where the matching comprises matching a surface region in the first 3D scan of the tooth with a corresponding surface region of the digital 3D shape of the post;
  virtually designing the post and core based on the virtual matching of the first 3D scan of the tooth and the digital 3D shape of the post.

The first 3D scan may be denoted the 3D scan in the following.

The 3D scan comprising at least part of the damaged tooth may comprise the outer part of the tooth and at least part of the inner part of tooth. The inner part of the tooth may be bore or cavity of the tooth, so scanning in the bore or cavity of the tooth may be obtained. In some cases the entire bore may be scanned, however in some cases the bore may be too deep and/or too narrow for obtaining a scan of the entire bore. Typically only part of the bore may be obtained by scanning into it. By matching the scan of the part of the bore with the digital 3D shape of the post, the entire bore may be derived or reconstructed by e.g combining the scan data and the digital 3D shape data, and the post of the post and core may be designed to fit the bore.

Use of Scan Pin

In some embodiments the digital 3D shape of the component is a digital 3D shape of a scan pin comprising an inner part and an outer part, where the outer part of the scan pin is located at least partly outside the tooth, and the inner part of the scan pin is located at least partly in the tooth, where the inner part of the scan pin corresponds to the post part.

It is an advantage that a scan pin can be used when scanning the damaged tooth for obtaining information to be able to virtually design the post and core. The inner part of the scan pin corresponds to the post of the post and core.

The digital 3D shape of the scan pin is a CAD file of the scan pin.

According to an aspect of the invention disclosed is a method of virtually designing a post and core restoration adapted for attachment in a damaged tooth of a patient, wherein the method comprises:
  obtaining a 3D image comprising a first 3D scan of at least part of the patient's set of teeth comprising the damaged tooth, where a scan pin comprising an outer part and an inner part is arranged in the tooth during the 3D scanning, such that the outer part of the scan pin is located at least partly outside the tooth, and the inner part of the scan pin is located at least partly in the tooth, where the inner part of the scan pin corresponds to the post of the post and core, and where the first 3D scan comprises the tooth and at least a part of the scan pin;
  providing a digital 3D shape of the scan pin comprising the outer part and the inner part of the scan pin;
  virtually matching the first 3D scan with the digital 3D shape of the scan pin, where the matching comprises matching the at least part of the scan pin of the first 3D scan with the at least part of the scan pin of the digital 3D shape, such that the inner part of the scan pin of the digital 3D shape is represented relative to the tooth in the first 3D scan;
  virtually designing the post and core based on the representation of the inner part of the scan pin relative to the tooth in the first 3D scan.

The first 3D scan may be denoted the 3D scan in the following. Where for an impression scan the at least part of the scan pin is the inner part corresponding to the post of the post and core, since the matching is performed by means of the inner part, which is the part which is scanned in an impression scan.

Where for an intra oral scan and a model scan the at least part of the scan pin is the outer part, since the matching is performed by means of the outer part, which is the part which is scanned in an intra oral scan and in a model scan.

According to the aspect regarding the use of a scan pin, a scan pin is, during scanning, arranged in a root canal or cavity of the tooth, where the post and core is adapted to be cemented afterwards.

It is an advantage to use a scan pin in the damaged tooth, while scanning for obtaining the exact position, orientation and placement of the bore and for measuring or gauging the bore's depth in the tooth, such that the post's position and depths in the tooth can be determined for virtually designing the post and core.

The 3D scan can be of the teeth directly in the mouth of the patient using an intra oral 3D scanner. Alternatively, the 3D scan can be of a physical model of the patient's teeth, such as a gypsum model made from an impression of the teeth. Alternatively, the 3D scan can be of an impression of the patient's teeth.

When scanning the teeth directly in the mouth of the patient or when scanning a physical model of the teeth, it is an advantage of the method that the inner part of the scan pin is represented by the 3D digital shape of the scan pin, because the inner part of the scan pin cannot be captured when scanning the surface of the teeth since the inner part is located inside the tooth and therefore not visible for a scanner performing a 3D surface scan.

When the 3D scanning is of an impression, it is an advantage of the method to use the digital shape of the inner part of the scan pin corresponding to the post because this digital 3D shape of the inner part of the scan pin may always be of a good data quality as it typically is from a CAD file of the scan pin. On the contrary, the 3D scan of the inner part of the scan pin may be in a less god data quality since it may be difficult to obtain a good scan of the inner part, as the inner part typically is a long and narrow spike. Thus the 3D scan of the inner part may comprise an uncertain surface, be noise-filled etc. So for the inner part of the scan pin, the digital 3D shape may be preferred to use instead of the 3D scan. Thus for an impression it is an advantage to use the digital 3D shape of the inner part of the scan pin instead of the 3D scan of the inner part of the scan pin, as the data quality of the digital 3D shape, typically CAD data, will typically be better than the data quality of the 3D scan.

That the inner part of the scan pin of the digital 3D shape is represented relative to the tooth in the first 3D scan may be understood as that the position, orientation, depth, placement, arrangement etc. of the inner part of the scan pin of the digital 3D shape is represented, determined, identified, derived, defined etc. relative to the tooth in the first 3D scan.

Thus the step of virtually designing the post and core based on the representation of the inner part of the scan pin relative to the tooth in the first 3D scan may be understood as virtually designing the post and core based on the position, orientation, depth, placement, arrangement etc. of the inner part of the scan pin relative to the tooth in the first 3D scan.

Matching by Means of Outer Part of Scan Pin

According to an aspect of the invention disclosed is a method of virtually designing a post and core restoration adapted for attachment in a damaged tooth of a patient, wherein the method comprises:
- obtaining a 3D image comprising a first 3D scan of at least part of the patient's set of teeth comprising the damaged tooth, where a scan pin comprising an outer part and an inner part is arranged in the tooth during the 3D scanning, such that the outer part of the scan pin is located at least partly outside the tooth, and the inner part of the scan pin is located at least partly in the tooth, where the inner part of the scan pin corresponds to the post of the post and core, and where the first 3D scan comprises the tooth and at least a part of the scan pin;
- providing a digital 3D shape of the scan pin comprising the outer part and the inner part of the scan pin;
- virtually matching the first 3D scan with the digital 3D shape of the scan pin, where the matching comprises matching the outer part of the scan pin of the first 3D scan with the outer part of the scan pin of the digital 3D shape, such that the inner part of the scan pin of the digital 3D shape is represented relative to the tooth in the first 3D scan;
- virtually designing the post and core based on the representation of the inner part of the scan pin relative to the tooth in the first 3D scan.

This aspect comprises where the scan is an intra oral scan of the teeth or a scan of the positive model of the teeth, since in these cases the matching of the 3D scan and the digital 3D shape is performed by matching the outer part of the scan pin in the two different representations. Thus impression scanning may not be included in this aspect.

In some embodiments the method further comprises: virtually deleting the outer part of the scan pin from the first 3D scan after the matching.

The visualization or representation of the post part or inner part of the scan pin relative to the tooth of the 3D scan may be improved by deleting the outer part of the scan pin.

In some embodiments virtually deleting the outer part of the scan pin from the first 3D scan comprises deleting points in an area surrounding the shape of the outer part of the digital 3D shape.

The points may also be triangles etc. The area surrounding the shape vicinity may be for example 20 micrometer around the surface or around the average position of the surface of the outer part. The reason for taking an area and not just along the surface, is that the surface may not be detected perfectly, there may noise in the scan ad therefore some uncertainty of the precise location of detected 3D points from scanning.

In some embodiments the method further comprises: performing virtual hole closing of the missing surface which arise after deletion of the outer part of the scan pin from the first 3D scan.

The hole closing may be curvature based for virtually closing the missing or lacking surface arising or occurring after the deletion.

In some embodiments the method further comprises: offsetting the surface of the 3D scan and/or the surface of the 3D digital shape to obtain a closed surface after deletion of the outer part of the scan pin.

The outer part of the scan pin may be deleted from the 3D scan and/or from the digital 3D shape.

In some embodiments representing the inner part of the scan pin of the digital 3D shape relative to the tooth in the first 3D scan comprises virtually providing the inner part of the scan pin from the 3D digital shape to the first 3D scan.

Providing may comprise adding, inserting etc.

In some embodiments virtually providing the inner part of the scan pin from the 3D digital shape to the first 3D scan comprises performing a Boolean subtraction of the inner part of the scan pin from the first 3D scan.

The post part or inner part of the scan pin can be Boolean subtracted because the position of the post part or inner part relative to the first 3D scan is known due to the matching of the outer part in the first 3D scan and in the 3D shape of the outer part from the digital 3D shape.

The 3D surface of the post part or inner part may be provided in the first 3D scan by means of the 3D shape of the post part or inner part from the digital 3D shape. Thus the post part or inner part in the digital 3D shape may be represented as a surface. For providing this surface in the first 3D scan, the surface is subtracted from the first 3D scan, because the post part or inner part is present inside the tooth corresponding to under the gingival or created surface of the first 3D scan. It may therefore be called a Boolean subtraction. Boolean subtraction may typically be used for points, but here it may also be used for surfaces. The surfaces may consist or comprise points.

The surface of the post part or inner part from the digital 3D shape is subtracted from the surface of the first 3D scan to obtain the groove like structure of the root canal corresponding to the post part or inner part of the scan pin in the tooth.

In some embodiments the method further comprises that the 3D image comprises a second 3D scan of at least part of the patient's set of teeth comprising the damaged tooth, where no scan pin is arranged in the tooth bore during the 3D scanning, and where the second 3D scan comprises at least part of a cavity of the tooth adapted for attachment of the post and core in the tooth.

It is an advantage that there is no component in the tooth, because the cavity and/or bore opening of the drilled hole can be seen. Since the drilled hole usually is long and narrow, the whole hole cannot be scanned, but the upper part of the hole may be scanned. By scanning the opening of the hole without the scan pin arranged, the exact shape of the hole opening can be obtained. When just scanning the scan pin in the tooth, it can be difficult to capture the exact detail at the interface or transition between the scan pin and the surface of the hole.

When only performing the first 3D scan it may be a problem to obtain the tooth cavity shape because the scan pin may block for the tooth cavity, so it may be an advantage also scanning the tooth cavity without the scan pin such that the view to the tooth cavity is good for the scanner, if scanning directly in the mouth or scanning a positive model.

In some embodiments the 3D image is a virtual combination of the first 3D scan comprising the tooth and the component with the second 3D scan only comprising the tooth.

If the 3D scan made down in the cavity or bore opening of the tooth does not capture the entire cavity or bore such as missing a part of the wall or the bottom, the digital 3D shape of the component or scan pin can be combined, matched, aligned etc. with the 3D scan of the tooth alone at the part where the cavity is captured and can be matched with the digital 3D shape. At the part where the first 3D scan is missing data about the scan pin, the digital 3D shape of the scan pin can be used so that a visualization of the entire cavity or bore canal can be obtained from which the post and core can be designed.

In some embodiments the method further comprises representing the scan pin comprising the outer part and the inner part relative to the damaged tooth in the second 3D scan.

In some embodiments the method further comprises: providing a transition between the surface of the tooth cavity from the second 3D scan and the surface of the scan pin from the digital 3D shape.

In some embodiments providing the transition between the surface of the tooth cavity from the second 3D scan and the surface of the scan pin from the digital 3D shape comprises performing hole closing of surface areas and/or offsetting of surfaces.

It is an advantage that the transition between the tooth cavity from the second scan and the post shape from the digital 3D shape can be made by hole closing or by offsetting where the scan surface and/or the digital 3D shape surface are deleted. The scan surface and the digital 3D shape may not meet, there may be empty space without any surface. So for bringing the surfaces together at a transition, the surfaces may be manipulated so that they can meet.

The transition must be made for each post if there are more posts in the post and core restoration.

In some embodiments the post and core restoration adapted for attachment in a damaged tooth comprises at least two posts, whereby the damaged tooth comprises at least two bores, and where a first post of the at least two posts is adapted for attachment in a first bore of the at least two bores, and where a second post of the at least two posts is adapted to attachment in a second bore of the at least two bores.

In some embodiments the method comprises obtaining a third 3D scan of at least part of the patient's set of teeth comprising the damaged tooth, where a first scan pin comprising an outer part and an inner part is arranged in the first bore during the 3D scanning, such that the outer part of the first scan pin is located at least partly outside the tooth, and the inner part of the first scan pin is located at least partly in the tooth, where the inner part of the first scan pin corresponds to the first post of the post and core, and where the third 3D scan comprises the tooth and at least part of the outer part of the first scan pin.

The terms "third" 3D and "fourth" 3D scan below are used because the terms "first" and "second" 3D scans have already been used previously for differentiating between a scan comprising the component and a scan without the component. The terms "third" and "fourth" 3D scan are used differentiating between a scan of a scan pin in one of the bores and a scan of a scan pin in another of the bores, and these scans are not meant to a number three or a number four scan after a number one and a number two scan.

In some embodiments the method comprises obtaining at fourth 3D scan of at least part of the patient's set of teeth comprising the damaged tooth, where a second scan pin comprising an outer part and an inner part is arranged in the second bore during the 3D scanning, such that the outer part of the second scan pin is located at least partly outside the tooth, and the inner part of the second scan pin is located at least partly in the tooth, where the inner part of the second scan pin corresponds to the second post of the post and core, and where the fourth 3D scan comprises the tooth and at least part of the outer part of the second scan pin.

In some embodiments the method comprises combining a third 3D scan of the tooth and the outer part of a first scan pin with a fourth 3D scan of the tooth and the outer part a second scan pin for designing the post and core comprising at least two posts.

In some embodiments the method comprises combining the third 3D scan of the tooth and the outer part of the first scan pin with the fourth 3D scan of the tooth and the outer part the second scan pin for designing the post and core comprising at least two posts.

In some embodiments the method comprises combining the third 3D scan and the fourth 3D scan of the tooth and the outer part of each of the scan pins for designing the post and core comprising at least two posts.

It is an advantage that the exact position and/or orientation and/or depth of each post in a post and core with multiple posts can be acquired by scanning scan pins in each bore, one at a time.

The software may automatically create the first post, and perfectly positioned and aligned insertion channels for the additional posts may be generated, thereby facilitating easy mounting of the restoration in the patient's mouth.

In some embodiments the method comprises virtually designing the post and core comprising at least two posts such that the at least two posts physically are configured to be inserted in the tooth.

In some embodiments virtually designing the post and core comprising at least two posts comprises:
- designing the core and the first post as one piece;
- designing the second post as a separate piece; and
- designing a through-hole in the core for insertion of the second post in the tooth through the core.

When a post and core comprises at least two posts i.e. multiple posts, the post and core shall be designed such that each of the posts can be inserted in its corresponding bore in the tooth. The insertion direction of the posts may be different, and therefore they may not be inserted simultaneously. In the case where the posts do not have the same insertion direction, one post may be integrated with the core and this post and core part may be inserted first. For inserting the other post(s) there may be through-hole(s) in the core such that the other post(s) can be inserted though the through-hole(s) in the core and all the way into the bore in the tooth.

In some embodiments the method comprises virtually designing the second post to have a length longer than its final length for fitting in it's bore and through the core for facilitating the insertion of the second post.

The second or other post(s) may be longer than its final length, since with a longer post it may be easier for the dentist to insert the post.

In some embodiments the method comprises virtually designing an indentation on the second post at the position where the second post protrudes from the core, when the second post is inserted in the second bore, and where the excess part of the second post protruding from the core is adapted to be removed at the indentation.

The part of the post sticking out of the core due to the long length, may be removed after insertion. However if the post is designed to have an indentation or notch where it is sticking out of the core, it may be easier to cut off, snap off, break off the excess part of the post, and the surface of the post may be easier to make level with the surface of the core.

In some embodiments a visible marker present on the scan pin uniquely identifies the shape of the post of the post and core.

It is an advantage because the post of the post and core should match the shape of the drill, which drilled the bore for the post, so if a standard post and core is used, then a standard drill may fit to this post, and by marking the type or size of the post and core on the scan pin, the dentist can easily and quickly find a matching drill for the scan pin and for the final post. The unique identification may be one or more numbers, one or more letters, one or more symbols, a combination of number(s), letter(s), dot(s), matrice(s), barcode(s) and/or symbol(s) etc. The unique identification or marker may be termed encoding.

The identification may for example be obtained by texture scanning or by scanning the geometry.

Advantageously by knowing the size and shape of the identification this can also be used to align the scan pin in the scan.

There exist at least three manufactures of post and cores and they may all have different sizes of their posts, so it is an advantage for the dental technician that he can determine from which manufacturer the scan pin post used in the scanning is from, just by looking on the 3D scan of the scan pin, and read off the dimensions, such as width and length. There may be different sizes of post also from the same manufacturer.

Alternatively, the dentist may first drill the bore in the tooth, and thereby the drill type determines the scan pin type and the final post type. In this case the dentist will select the scan pin corresponding to the drill he used, and the dental technician can then determine from the 3D scan showing the scan pin which post to select.

In some embodiments the first 3D scan is obtained before the second 3D scan.

In some embodiments the second 3D scan is obtained before the first 3D scan.

The second 3D scan can be performed before or after the first 3D scanning of the component comprising the scan pin and the post member in the tooth. The terms "first" 3D scan and "second" 3D scan does not determine the order of which the scans may be obtained, the terms first and second are used to distinguish the two different scans. The person performing the scans, e.g. a dental technician, a dentist etc, may scan in the order he/she prefers. If the person prefers scanning the component in the tooth before scanning the tooth without the component this can be done as well as scanning the tooth without the component before scanning the tooth with the component.

In some embodiments the first 3D scan or the second 3D scan comprises the damaged tooth, the outer part of the scan pin, if the scan pin is inserted in the tooth, and at least one or more neighbor teeth or the neighborhood, if no teeth as neighbors.

It is an advantage that the patient's entire set of teeth may be scanned in this scan or at least the neighbor teeth besides the damaged tooth and any scan pin.

In some embodiments the second 3D scan or the first 3D scan comprises only at least part of the damaged tooth, and the outer part of the scan pin, if the scan pin is inserted in the tooth.

Thus this scan comprises only the area where there is a change relative to the scan where the neighbor teeth were also scanned.

It is an advantage that the neighbor teeth need not be scanned in both scans, as the neighbor teeth does not change during the scanning, only the damaged tooth is changed when the scan pin is inserted or not. Thus only the difference is scanned in this scan. Furthermore an area may be deleted in one scan and replaced with difference from the other scan. Hereby scan time is saved.

In some embodiments the 3D scan obtained first comprises the damaged tooth, the outer part of the scan pin, if the scan pin is inserted in the tooth, and at least one or more neighbor teeth.

Thus the first performed scan may be the scan comprising the most, i.e. also neighbor teeth.

In some embodiments the 3D scan obtained secondly comprises only the damaged tooth, and the outer part, if the scan pin is inserted in the tooth. The 3D scan first obtained may typically also be of the surroundings of the tooth, e.g. one or more neighbor teeth or the whole arch or the antagonist etc. The 3D scan obtained secondly, i.e. after the first obtained 3D scan, may typically be of only the tooth and the component, if present, which should be the only place where a change is made, namely whether the scan pin is inserted or not.

In some embodiments virtually designing the post and core comprises providing a cement gap relative to the post part and/or relative to the core part.

In some embodiments virtually designing the post and core comprises providing a tapering angle of the core.

In some embodiments virtually designing the post and core comprises providing an anatomic top of the core for fitting to the anatomy of the crown.

In some embodiments virtually designing the post and core comprises providing an anatomic top of a coping for fitting to the anatomy of the crown.

In some embodiments virtually designing the post and core comprises defining a distance from the core to the top of the crown.

In some embodiments virtually designing the post and core comprises automatically generating the core.

When designing the restoration, i.e. the post and core, coping, crown etc., automatic virtual wax block out may also be performed.

Based on the crown design, the user may set a post and core margin line and the software may automatically generate a corresponding post and core design, including block-out and cement gap for the post. The core shape may be adjusted using 3D handles and flexible sculpt tools. The single workflow may be completed by designing the coping and the anatomy of the crown on top of the post or add attachments to combine with removable partials.

In some embodiments designing a crown for the post and core comprises blocking out areas identified as undercuts.

In some embodiments designing a crown for the post and core comprises offsetting the shape of the core.

In some embodiments designing the core comprises offsetting the crown.

In some embodiments designing a crown for the post and core comprises providing margins lines for the core and/or for a coping and/or for the crown.

In some embodiments virtually designing the post and core comprises designing the crown before designing the post and core.

In some embodiments virtually designing the post and core comprises designing the post and core before designing the crown.

In some embodiments virtually designing the post and core comprises designing a coping between designing the crown and the post and core.

In some embodiments virtually designing the post and core comprises:
  designing the crown first,
  designing the post and core secondly, and
  designing the coping finally.

In some embodiments the post part of the scan pin and the drill which drilled the bore in the tooth have similar shapes.

In some embodiments the post is designed to have a shape similar to the post part of the scan pin and/or to the drill which drilled the bore in the tooth.

It is an advantage of the embodiments that when a drill drilled the bore in the tooth and the post member has the same shape and size as the drill, then the post member should fit perfectly in the bore, at least if the bore was held straight when drilling was made.

Because if may be difficult for the dentist to hold the drill perfectly straight when drilling, the second 3D scan may be performed to capture the opening of the hole, whereby a potential non-straight drilling can be accounted for.

In some embodiments obtaining a 3D scan of at least part of the patient's set of teeth comprises performing a 3D scanning intra orally of the patient using an intra oral scanner.

In some embodiments obtaining a 3D scan of at least part of the patient's set of teeth comprises performing a 3D scanning of a physical model of the patient's teeth in a desktop scanner or using an intra oral scanner.

In some embodiments obtaining a 3D scan of at least part of the patient's set of teeth comprises performing a 3D scanning of a physical impression of the patient's teeth in a desktop scanner or using an intra oral scanner.

In some embodiments the 3D scan is a surface scan.

In some embodiments the 3D scan is a CT scan.

In some embodiments the 3D scan is performed by means of laser light scanning, white light scanning, probe-scanning, X-ray scanning, and/or CT scanning.

Scan pins for use in designing post and core restorations are disclosed herein.

Accordingly, in one aspect the description relates to a scan pin for determining the position, depth and/or orientation of a bore drilled in a damaged tooth of a patient, the scan pin comprises a scan head and a scan post extending from the scan head wherein the shape of the scan post in at least one area corresponds to the shape of at least a part of the working surface shape of a drill used to drill the bore.

Such a scan pin is particularly advantageous in a method for virtually designing a post and core restoration as described herein.

Moreover, the scan pin fit securely and precisely in the bore and thus the position, depth and/or orientation of a bore drilled in the jaw bone may advantageously be accurately determining.

Alternatively the shape of the scan post in at least one area corresponds to the shape of the bore.

It should be understood herein that the working surface shape of a drill is the shape that the drill creates when drilling. I.e. the drill may have cutting edges or a rough surface having a diamond abrasive coating but these irregularities will not be present in the finally drilled bore.

As described disclosed herein the scan head may correspond to an outer part of the scan pin which is arranged at least partly outside the tooth and the scan post may correspond to an inner part of the scan pin which is arranged at least partly inside the bore of the tooth.

Preferably the shape of the entire scan post corresponds to the working surface shape of the drill used to drill the hole.

In one embodiment at least the tip area of the scan post, opposite the scan head, corresponds to the working surface area of a part of the drill.

In one embodiment the scan post has a tapering diameter. The diameter typically decreases in the direction from the scan head, providing a shape that corresponds to the drill.

Typically the scan pin is solid, e.g. having no through going bores, and/or formed without threads.

In another aspect, the scan pin comprising a scan head and a scan post is provided in a kit together with at least a post drill for drilling the post bore. The kit may furthermore comprise a gauge to check the fit and orientation of the final post, a root facer to produce a flat surface to seat the post head to, the post itself and/or a driver wherein the post can be mounted and used to arrange the post into place.

The scan pin may advantageously comprise one or more of the features as described herein.

In yet another aspect as discussed herein a model system comprising a dental model and at least one die, wherein a first bore section is provided in the die and a second bore section is provided in the model, wherein the first bore section and the second bore section are co-axially aligned when the die is arranged correctly in the dental model.

This has the effect that even though neighboring teeth or other structure prevent for the entire bore to be contained in the die it is possible to provide a solution where post and core model can be placed in the model system.

3D Modeling

The virtual designing of the post and core may be denoted or comprise 3D modeling. 3D modeling is the process of developing a mathematical, wireframe representation of any three-dimensional object, called a 3D model, via specialized software. Models may be created automatically, e.g. 3D models may be created using multiple approaches: use of NURBS curves to generate accurate and smooth surface patches, polygonal mesh modeling which is a manipulation of faceted geometry, or polygonal mesh subdivision which is advanced tessellation of polygons, resulting in smooth surfaces similar to NURBS models.

Intra Oral Scanning

The 3D scans may be intra oral scans, which may be obtained by means of an intra oral scanner. The intra-oral scanner may be configured for utilizing focus scanning, where the digital 3D representation of the scanned teeth is reconstructed from in-focus images acquired at different focus depths. The focus scanning technique can be performed by generating a probe light and transmitting this probe light towards the set of teeth such that at least a part of the set of teeth is illuminated. Light returning from the set of teeth is transmitted towards a camera and imaged onto an image sensor in the camera by means of an optical system, where the image sensor/camera comprises an array of sensor elements. The position of the focus plane on/relative to the set of teeth is varied by means of focusing optics while images are obtained from/by means of said array of sensor elements. Based on the images, the in-focus position(s) of each of a plurality of the sensor elements or each of a plurality of groups of the sensor elements may be determined for a sequence of focus plane positions.

The in-focus position can e.g. be calculated by determining the light oscillation amplitude for each of a plurality of the sensor elements or each of a plurality of groups of the sensor elements for a range of focus planes. From the in-focus positions, the digital 3D representation of the set of teeth can be derived.

Scanning of Models and Impressions

The 3D scans of models or impressions may be obtained by means of a desktop 3D scanner. Obtaining a three dimensional representation of the surface of an object by scanning the object in a 3D scanner can be denoted 3D modeling, which is the process of developing a mathematical representation of the three-dimensional surface of the object via specialized software. The product is called a 3D model. A 3D model represents the 3D object using a collection of points in 3D space, connected by various geometric entities such as triangles, lines, curved surfaces, etc. The purpose of a 3D scanner is usually to create a point cloud of geometric samples on the surface of the object.

3D scanners collect distance information about surfaces within its field of view. The "picture" produced by a 3D scanner describes the distance to a surface at each point in the picture.

For most situations, a single a scan or sub-scan will not produce a complete model of the object. Multiple sub-scans, such as 5, 10, 12, 15, 20, 30, 40, 50, 60, 70, 80, 90 or in some cases even hundreds, from many different directions may be required to obtain information about all sides of the object. These sub-scans are brought in a common reference system, a process that may be called alignment or registration, and then merged to create a complete model.

A triangulation 3D laser scanner uses laser light to probe the environment or object. A triangulation laser shines a laser on the object and exploits a camera to look for the location of the laser dot. Depending on how far away the laser strikes a surface, the laser dot appears at different places in the camera's field of view. This technique is called triangulation because the laser dot, the camera and the laser emitter form a triangle. A laser stripe, instead of a single laser dot, may be used and is then swept across the object to speed up the acquisition process.

Structured-light 3D scanners project a pattern of light on the object and look at the deformation of the pattern on the object. The pattern may be one dimensional or two dimensional. An example of a one dimensional pattern is a line. The line is projected onto the object using e.g. an LCD projector or a sweeping laser. A camera, offset slightly from the pattern projector, looks at the shape of the line and uses a technique similar to triangulation to calculate the distance of every point on the line. In the case of a single-line pattern, the line is swept across the field of view to gather distance information one strip at a time.

An example of a two-dimensional pattern is a grid or a line stripe pattern. A camera is used to look at the deformation of the pattern, and an algorithm is used to calculate the distance at each point in the pattern. Algorithms for multistripe laser triangulation may be used.

Iterative Closest Point

Iterative Closest Point (ICP) is an algorithm employed to minimize the difference between two clouds of points. ICP can be used to reconstruct 2D or 3D surfaces from different scans or sub-scans. The algorithm is conceptually simple and is commonly used in real-time. It iteratively revises the transformation, i.e. translation and rotation, needed to minimize the distance between the points of two raw scans or sub-scans. The inputs are: points from two raw scans or sub-scans, initial estimation of the transformation, criteria for stopping the iteration. The output is: refined transformation. Essentially the algorithm steps are:

1. Associate points by the nearest neighbor criteria.
2. Estimate transformation parameters using a mean square cost function.
3. Transform the points using the estimated parameters.
4. Iterate, i.e. re-associate the points and so on.

The present invention relates to different aspects including the method described above and in the following, and corresponding methods, devices, apparatuses, systems, uses, kits and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, disclosed herein is a computer program product comprising program code means for causing a data processing system to perform the method according to any of the embodiments, when said program code means are executed on the data processing system, and a computer program product, comprising a computer-readable medium having stored there on the program code means.

Disclosed is a non-transitory computer readable medium storing thereon a computer program, where said computer program is configured for causing a computer-assisted method of virtually designing a post and core restoration adapted for attachment in a damaged tooth of a patient, where the damaged tooth comprises a bore for receiving the post of the post and core, wherein the method comprises:

obtaining a 3D image comprising a first 3D scan comprising at least a part of the damaged tooth;

providing a digital 3D shape of at least a part of a component adapted for fitting to the damaged tooth, where the component comprises at least a post part adapted for fitting in the bore of the damaged tooth;

virtually matching the first 3D scan of the tooth and the digital 3D shape of the component, where the matching comprises matching a surface region in the first 3D scan of the tooth with a corresponding surface region of the digital 3D shape component, such that at least part of the post part of the digital 3D shape of the component is represented relative to the first 3D scan of the tooth;

virtually designing the post and core restoration based on the representation of the post part of the digital 3D shape of the component relative to the first 3D scan of the tooth.

In particular, disclosed herein is a system for virtually designing a post and core restoration adapted for attachment in a damaged tooth of a patient, where the damaged tooth comprises a bore for receiving the post of the post and core, wherein the system comprises:

means for obtaining a 3D image comprising a first 3D scan comprising at least a part of the damaged tooth;

means for providing a digital 3D shape of at least a part of a component adapted for fitting to the damaged tooth, where the component comprises at least a post part adapted for fitting in the bore of the damaged tooth;

means for virtually matching the first 3D scan of the tooth and the digital 3D shape of the component, where the matching comprises matching a surface region in the first 3D scan of the tooth with a corresponding surface region of the digital 3D shape component, such that at least part of the post part of the digital 3D shape of the component is represented relative to the first 3D scan of the tooth;

means for virtually designing the post and core restoration based on the representation of the post part of the digital 3D shape of the component relative to the first 3D scan of the tooth.

The means for obtaining a first 3D scan may a 3D surface scanner, such as an intra oral scanner, a desktop scanner etc. The 3D scan may be loaded into and visualized in a software program or the system, and in this software program or system the 3D scan can be modeled and virtually designed.

The means for providing a digital 3D shape of a component may be a digital library or a digital file comprising digital 3D shapes, such as CAD files, of the component. The digital library and the digital file can be loaded into the software program or system where the 3D scan is visualized.

The means for virtually matching the 3D scan and the digital 3D shape may be processing means in the software program or system.

The means for virtually designing the post and core restoration may be processing means in the software program or system.

In some embodiments, the system comprises a nontransitory computer readable medium having one or more computer instructions stored thereon, where said computer instructions comprises instructions for carrying out a method of virtually designing a post and core restoration adapted for attachment in a damaged tooth of a patient, where the damaged tooth comprises a bore for receiving the post of the post and core, wherein the method comprises:

obtaining a 3D image comprising a first 3D scan comprising at least a part of the damaged tooth;

providing a digital 3D shape of at least a part of a component adapted for fitting to the damaged tooth, where the component comprises at least a post part adapted for fitting in the bore of the damaged tooth;

virtually matching the first 3D scan of the tooth and the digital 3D shape of the component, where the matching comprises matching a surface region in the first 3D scan of the tooth with a corresponding surface region of the digital 3D shape component, such that at least part of the post part of the digital 3D shape of the component is represented relative to the first 3D scan of the tooth;

virtually designing the post and core restoration based on the representation of the post part of the digital 3D shape of the component relative to the first 3D scan of the tooth.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIGS. 4A-4B show examples of the coping and crown design in a screenshot from a virtual environment where the virtual design can be performed by means of software program(s).

FIGS. 5A-5H show examples of scanning at least part of the bore and/or the bore opening or cavity in the damaged tooth, and designing a post and core based on the scan.

FIGS. 7A-7H show examples of post and cores with multiple posts.

FIGS. 14A-14D and 15A-15D show example embodiment of the scan pins with dimensions in millimeters.

DETAILED DESCRIPTION

In the following description, reference is made to the accompanying figures, which show by way of illustration how the invention may be practiced.

Figure 1A:
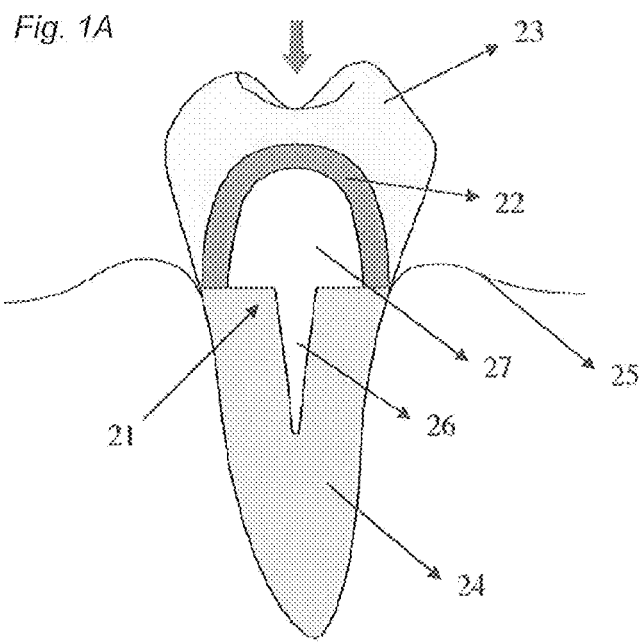
FIGS. 1A and 1B show prior art examples of post and cores.
Figure 1B:
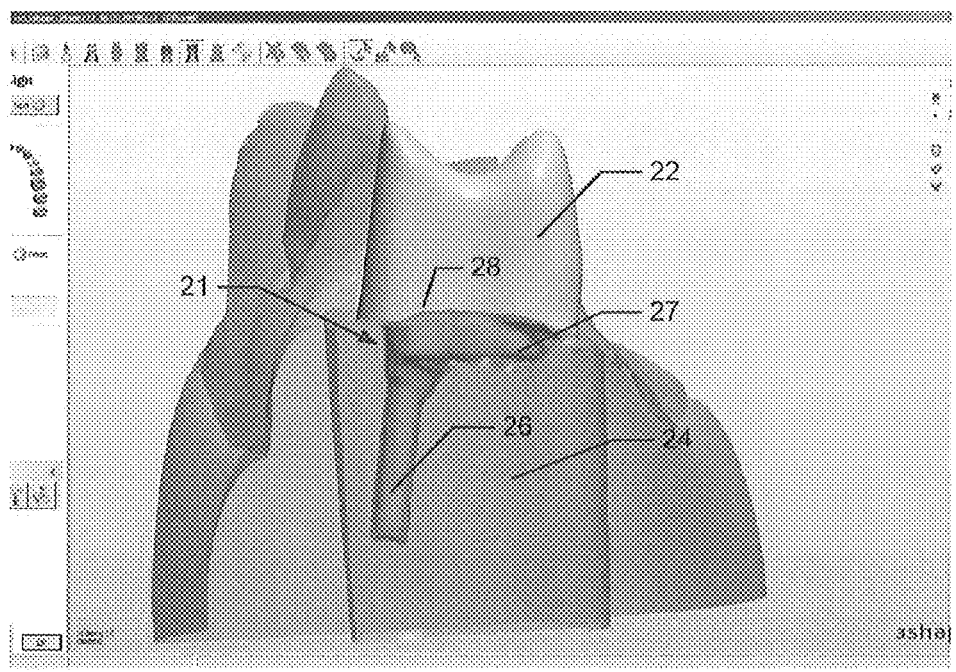

FIGS. 1A and 1B show examples of post and cores.

FIG. A shows a schematic example of a restoration comprising a post and core. The post and core 21 comprises the post 26 entering and matching the bore of the tooth 24 and the core 27 that provides retention of the coping 22 and the crown 23. The damaged tooth 24 has been prepared, i.e. it has been grinded down close to the gingival 25 and a bore has been provided by means of a dental drill. The post and core 21 matches the bore of the prepared tooth 24. The post and core 21 also provides retention/support for the coping 22 and the crown 23. The post and core 21, the coping 22 and the crown 23 can all be designed/provided according to the method.

FIG. 1B shows an example of a screenshot from a software program where a post and core can be virtually designed.

The post 26 is arranged in the bore of the damaged tooth. The core 27 is also present at least partly in the tooth. The edge 28 indicates what is present below the gingival and thereby not visible for the human eye, and what is present above the gingival and thereby visible for the human eye. A coping 22 is designed around the core 27.

Figure 2:
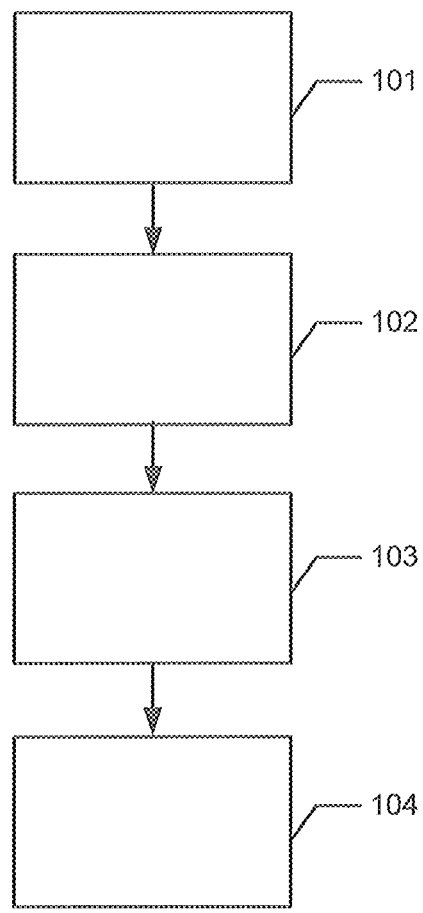
FIG. 2 shows an example of a flowchart of a method of virtually designing a post and core restoration adapted for attachment in a damaged tooth of a patient, where the damaged tooth comprises a bore for receiving the post of the post and core.

FIG. 2 shows an example of a flowchart of a method of virtually designing a post and core restoration adapted for attachment in a damaged tooth of a patient, where the damaged tooth comprises a bore for receiving the post of the post and core.

In step 101a first 3D scan comprising at least a part of the damaged tooth is obtained. The 3D scan may be obtained by means of a scanner, such as a surface scanner. The scanner can be an intra oral scanner for scanning directly in the mouth of the patient, or the scanner can be a desktop scanner for scanning an impression of the patient's teeth or scanning a positive working model of the patient's teeth, where the positive working model may be poured in gypsum other suitable plaster material from an impression. A dentist may perform the intra oral scanning in a dental clinic. A dental technician may perform the impression or positive model scanning in a dental laboratory. The 3D scan provides a 3D representation of the damaged tooth, which can be used and/or manipulated in a software program to virtually design the post and core.

In step 102 a digital 3D shape of at least a part of a component adapted for fitting to the damaged tooth is provided, where the component comprises at least a post part adapted for fitting in the bore of the damaged tooth. The digital 3D shape of at least part of a component may be a CAD file of the component comprising 3D information of the component. The component comprises at least a post part adapted for fitting in the bore of the damaged tooth. The component may the post of the post and core, i.e. the digital 3D shape may be a CAD file of the post. Alternatively, the component may be a scan pin, which is configured for being inserted in the damaged tooth while the damaged tooth is scanned. The scan pin comprises a post part which is adapted to be inserted in the bore of the tooth during scanning, thus the digital 3D shape may a CAD file of the scan pin.

In step 103 the first 3D scan of the tooth and the digital 3D shape of the component is matched, where the matching comprises matching a surface region in the first 3D scan of the tooth with a corresponding surface region of the digital 3D shape component, such that at least part of the post part of the digital 3D shape of the component is represented relative to the first 3D scan of the tooth. The matching may be a virtual matching performed in the software program. The matching may comprise aligning, overlaying, combining etc. the first 3D scan of the tooth and the digital 3D shape of the component. The matching is performed on corresponding parts of the 3D scan of the tooth and the digital 3D shape. The corresponding part or surface region of the 3D scan may be at least part of the post part, if for example the first 3D scan comprises at least part of the bore of the tooth, which can be obtained by scanning into the bore in the tooth in the mouth, or scanning into the bore in the tooth in the positive model, or scanning the post part of the scan pin in an impression scan. The post part is then matched with the post part of the digital 3D shape. Alternatively, the corresponding part or surface region of the 3D scan may be at least part of the outer part of the scan pin, if for example the 3D scan comprises at least part of the outer part of the scan pin, which can be obtained by scanning the tooth when the scan pin is inserted in the tooth in the mouth of the patient, or by scanning the tooth when the scan pin is inserted in the tooth of the positive model.

In step 104 the post and core restoration is virtually designed based on the representation of the post part of the digital 3D shape of the component relative to the first 3D scan of the tooth. Since the at least part of the post part of the digital 3D shape of the component is represented relative to the first 3D scan of the tooth, this can be used to design the post and core, since when knowing the exact position, orientation, depth etc that the post should have in the tooth for providing a good retention, the final post and the final core fitting to the post and to the remainder of the tooth structure can be designed to obtain a perfectly fitting post and core with good retention and strength.

FIGS. 3A-3I show a schematic examples of virtually designing a post and core by means of a scan pin. The figures are in 2D but it is understood that virtually designing a post and core is performed in a 3D virtual environment by use of a software program.

Figure 3A:
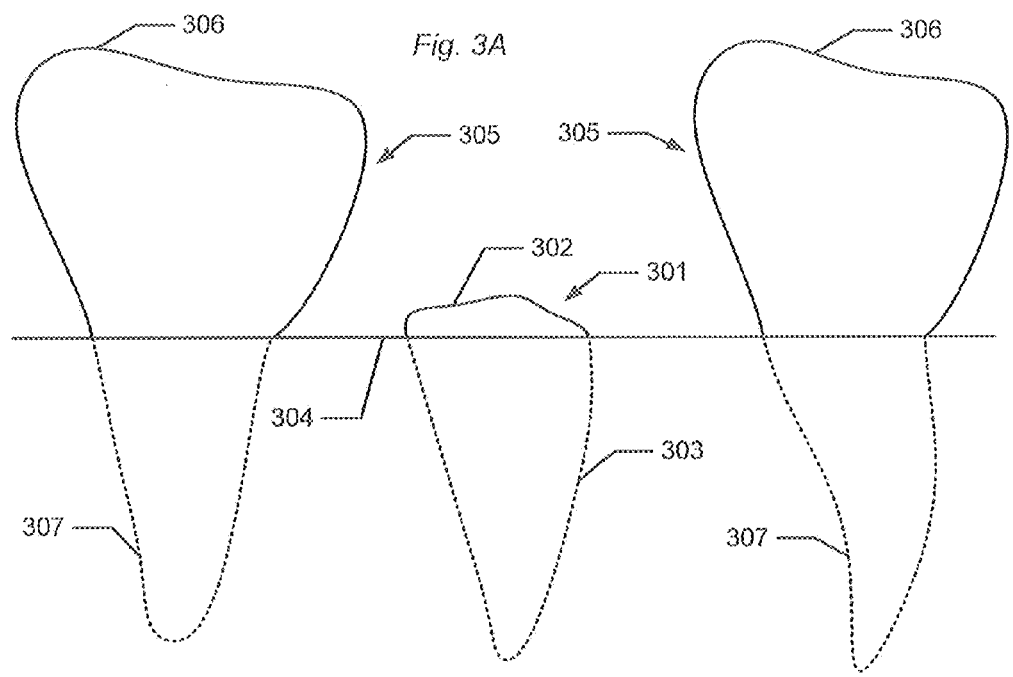
FIGS. 3A-3I show a schematic examples of virtually designing a post and core by means of a scan pin.

FIG. 3A shows an example of a set of teeth from a patients mouth comprising two healthy teeth 305 each comprising a natural crown 306 and a root 307 and a damaged tooth 301. The natural crown of the tooth is damaged, so only a small tooth structure 302 is present above the gingival 304. The root 303 of the tooth is present below the gingival 304. The root 303 may require a root treatment or an endodontic procedure. The crown of the tooth may have been damaged before the patient sees the dentist or the dentist may damaged or grind the crown away to obtain the small tooth structure 302 such that root treatment or the like can easily be performed. The work performed by the dentist may not be a part of the present method.

The parts of the teeth 301, 305 present below the gingival is marked with dotted line, since these parts are not visible for a 3D surface scanner.

Figure 3B:
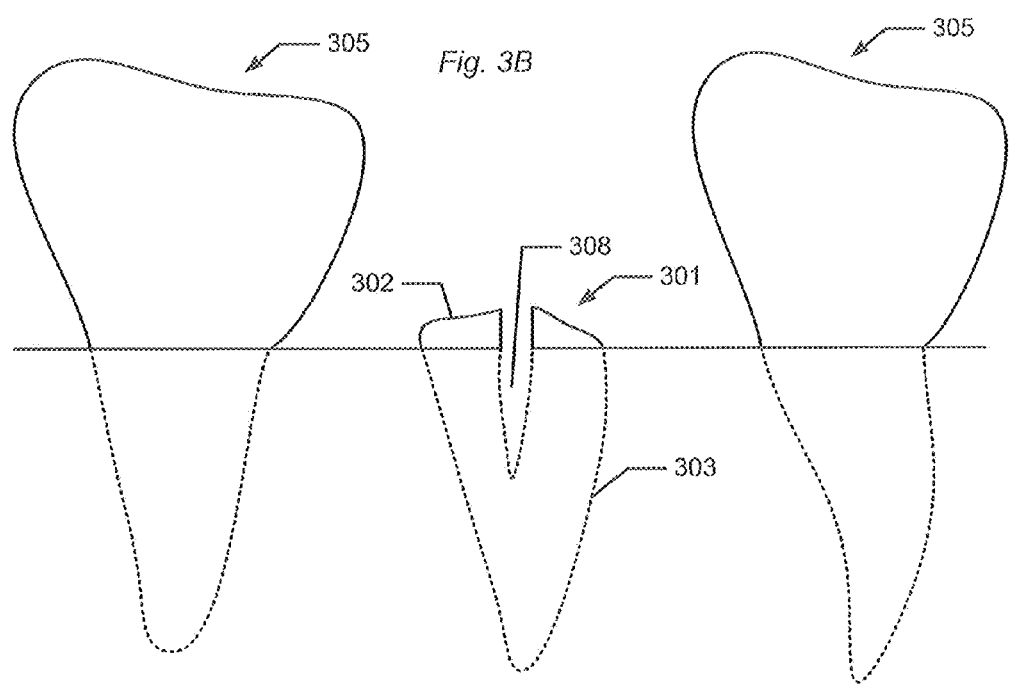

FIG. 3B shows an example of the tooth 301 after the dentist has drilled a bore 308 in the tooth 301. The bore 308 passes the visible tooth structure 302 and down into the root 303 of the tooth 301.

The bore 308 may be have been drilled using a drill, and the post of the post and core may correspond to the drill, such that the post exactly matches the bore. That is the post may have the exact same shape and size of the drill, or the post may have the same shape but be a little bit smaller, such there is room for a cement space in the root 303 for attaching the post.

Figure 3C:
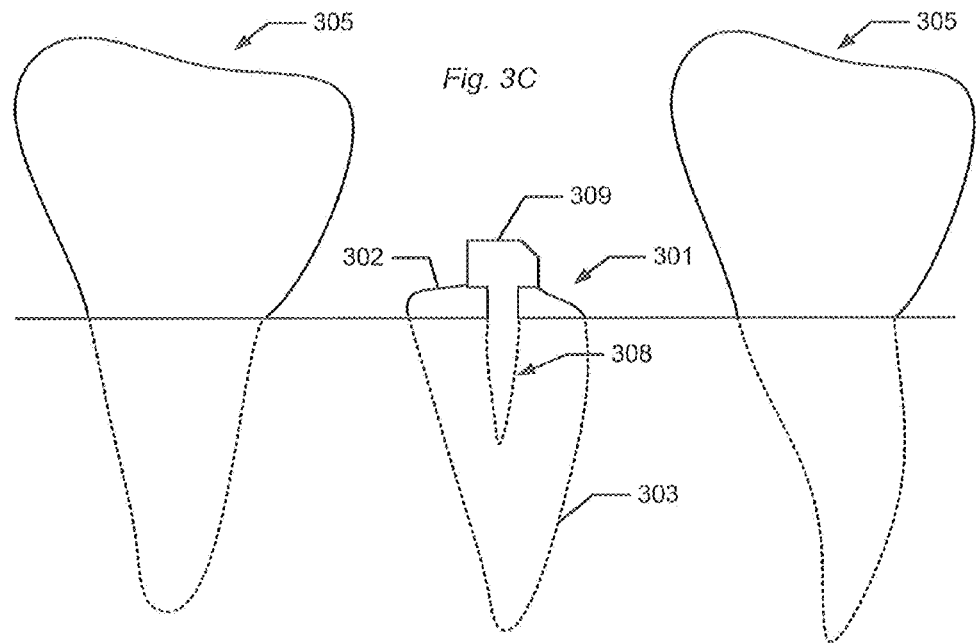

FIG. 3C shows an example where a scan pin 309 is inserted in the tooth 301 when the tooth is scanned. The scan pin is visible above the tooth structure 302, passes through the tooth structure 302, and extends down into the bore 308. The tooth 301 can now be scanned, while the scan pin 309 is arranged in the tooth. The post part of the scan pin 309 which is present in the bore 308 may exactly match or fit in the bore 308 such that the scan pin 309 is firmly arranged in the bore 308 and is unable to move from side to side, whereby the 3D scan of the scan pin 309 in the tooth 301 may provide an exact representation of the relative position, orientation, arrangement etc. between the scan pin 309 and the tooth 301.

Figure 3D:
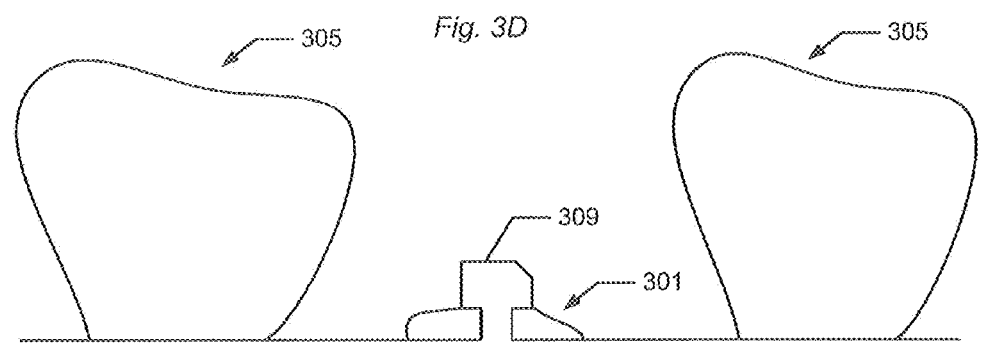

FIG. 3D shows a schematic example of a 3D scan of the set of teeth comprising the damaged tooth 301, when the scan pin 309 is inserted in the tooth 301 during scanning. The tooth roots are not visible in a 3D surface scan. The neighbor teeth 305 are also seen in the 3D scan, and they may be used when designing the final crown around the core of the post and core, since the final crown on the damaged tooth 301 should fit to the natural crowns of the neighbor teeth 305.

Figure 3E:
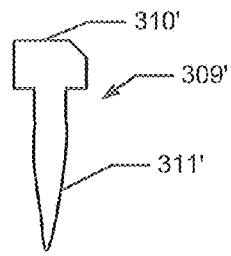

FIG. 3E shows an example of a digital 3D shape 309' of the scan pin. The digital 3D shape 309' of the scan pin comprises an outer part 310' which is adapted to be arranged at least partly outside the tooth 301 such that it is visible for a 3D surface scanner, and an inner part 311' which is adapted to be arranged at least partly inside the tooth 301 in the bore, and the inner part 311' corresponds to the post of the post and core. The digital 3D shape 309' of the scan pin may be a CAD file of the scan pin.

Figure 3F:
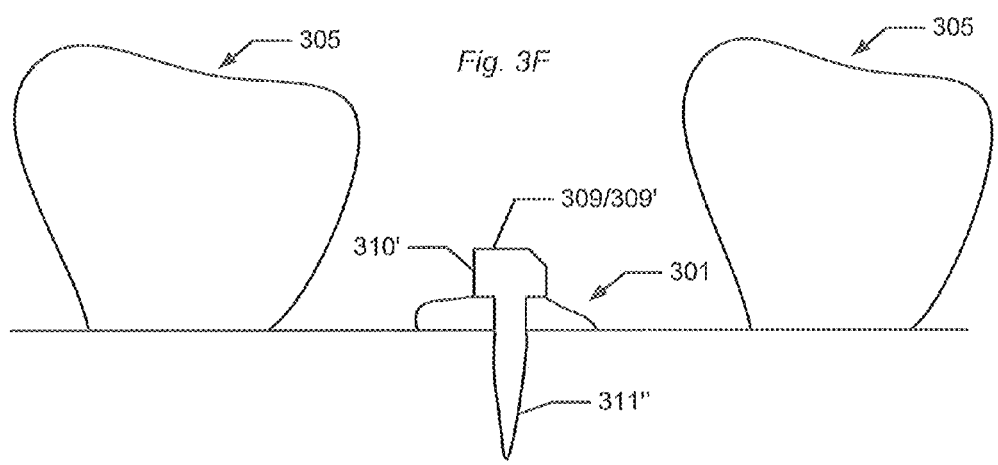

FIG. 3F shows an example where the digital 3D shape 309' of the scan pin from FIG. 3E is matched to the scan pin 309 in the 3D scan of the tooth 301 and the scan pin 309 from FIG. 3d).

Figure 3G:
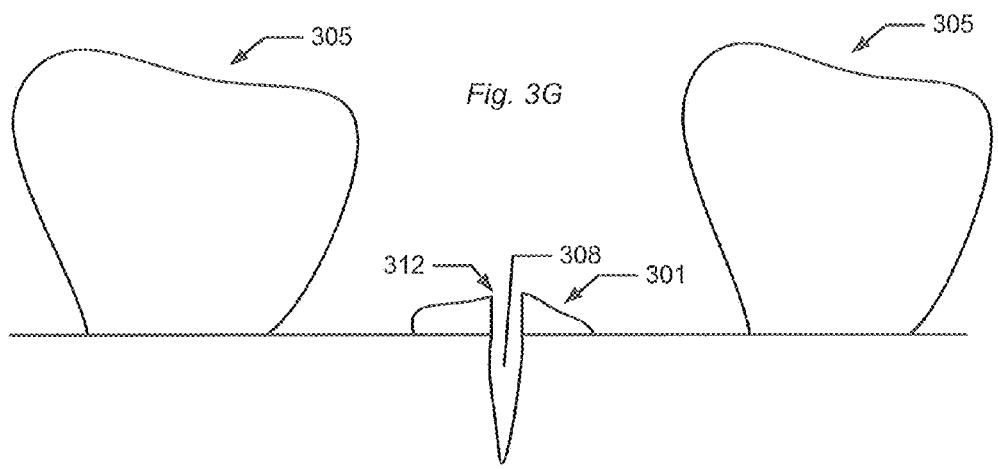

FIG. 3G shows an example where a second 3D scan is obtained of the tooth 301 without the scan pin inserted. The second 3D scan of the tooth 301 may be obtained to capture the details at the bore opening 312 or cavity which may be hidden by the scan pin in the first 3D scan as seen in FIG. 3D. The bore opening may be an advantage to obtain such that the core can be designed to exactly fit the tooth structure 302 at the bore opening 312. It may not be a requirement to obtain the second 3D scan as shown in FIG. 3G for performing the method of the invention.

Figure 3H:
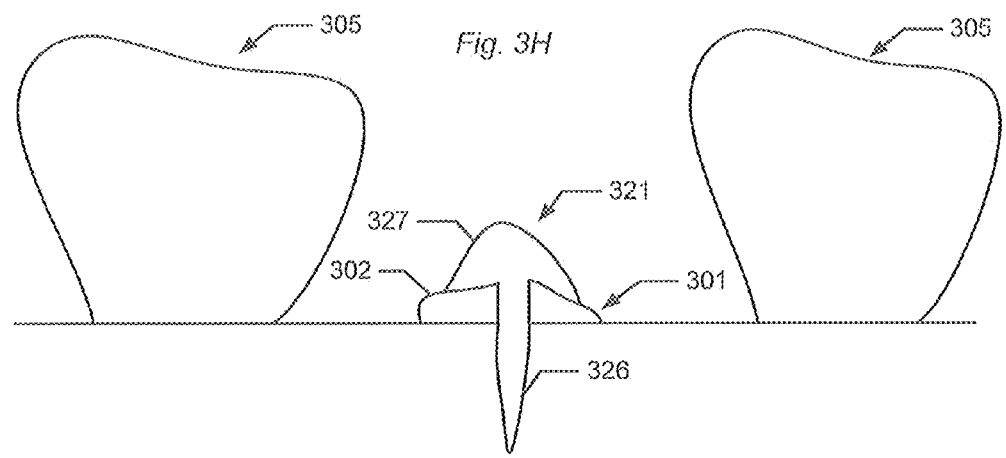

FIG. 3H shows an example of the virtually designed post and core 321 relative to the tooth 301, where the post and core 321 comprises a post 326 adapted to be arranged in the bore of the tooth 301 and a core adapted to be present outside and following and corresponding to the remaining tooth structure 302.

Figure 3I:
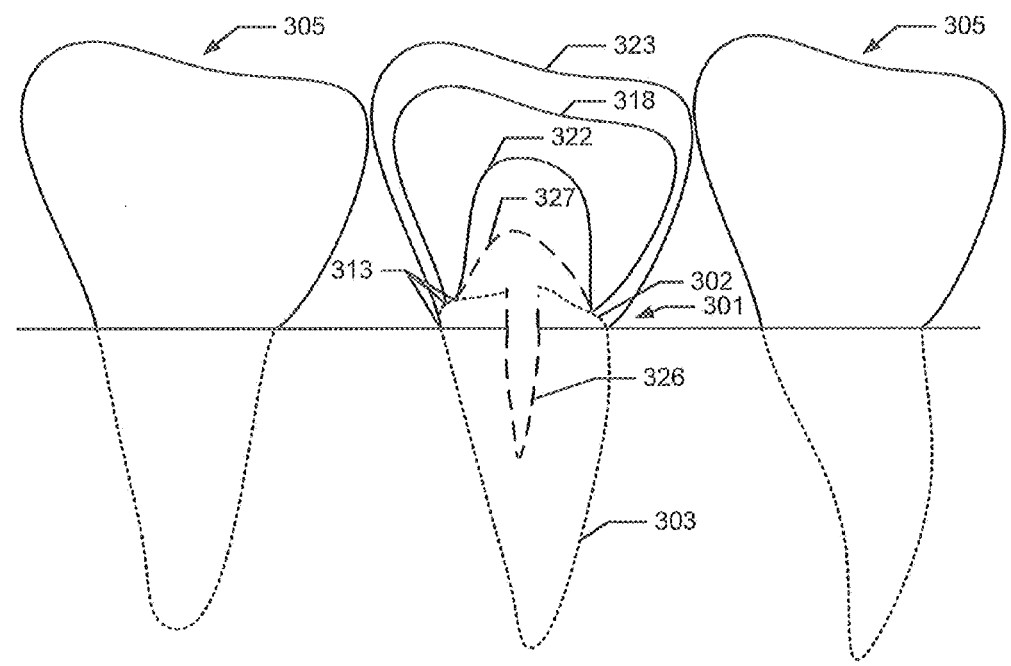

FIG. 3I shows an example where all the layers of a final crown is virtually designed. A coping 322 is designed around the core 327 of the post and core 321. An crown 323 is designed around the coping 322. An extra coping 318 may be provided, and the crown 323 may be a veneering layer in the coping 318 or 322. The sequence or order in which the different parts of the restoration may be different than suggested above. For example the crown 323 may be designed first, and the coping 318 and/or 322 and/or the core 327 may then be designed afterwards. It is understood that the attachment points or margin line 313 of the different parts of the restoration, e.g. the coping(s) and the crown, may be arranged differently than shown in the figure.

FIGS. 4A-4B show examples of the coping and crown design in a screenshot from a virtual environment where the virtual design can be performed by means of software program(s).

FIG. 4A shows an example of a coping 422 and crown 423 seen from the front of the teeth.

FIG. 4B shows an example of the coping 422 and crown 423 seen from a proximal surface of the tooth.

It is seen that the coping 422 resembles the anatomy of the crown.

FIGS. 5A-5H show examples of scanning at least part of the bore and/or the bore opening or cavity in the damaged tooth, and designing a post and core based on the scan.

The scan of the bore and/or of the bore opening or cavity may be used as a second scan to combine with the first 3D scan as illustrated in the FIGS. 3A-3I, resembling the scan shown in FIG. 3G.

Alternatively the scan of the bore may stand alone, i.e. not be combined with the first scan, if the scan of the bore is good enough for performing a matching of a post part with the representation of the bore obtained from the scan.

Figure 5A:
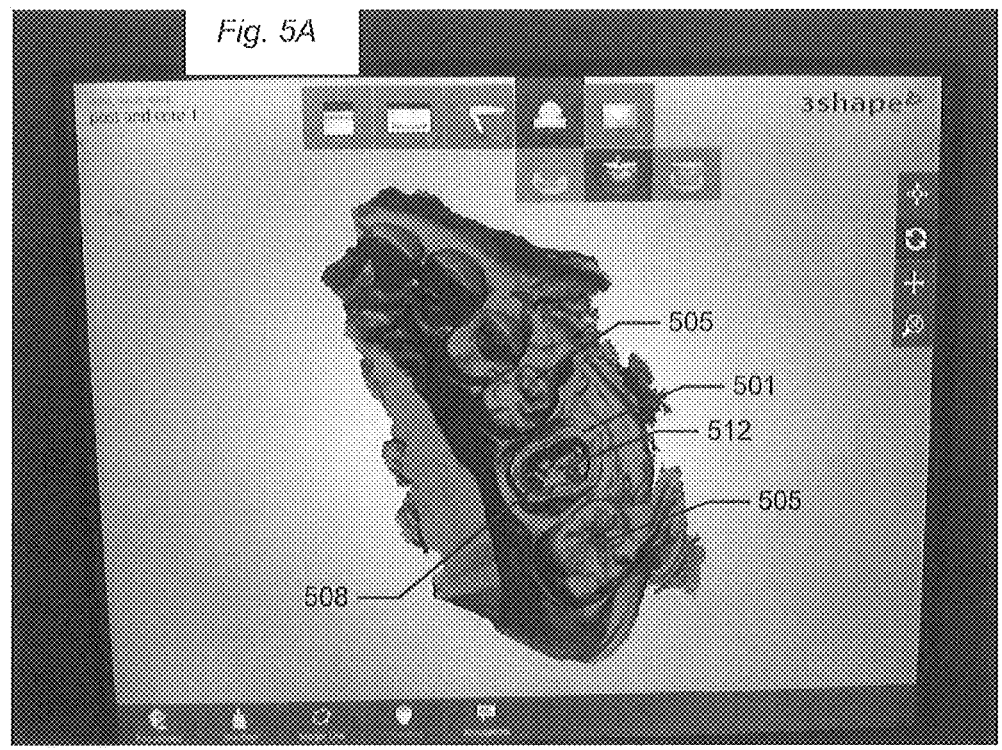

FIG. 5A shows an example of a screenshot of a 3D scan of a bore opening or cavity 512 of a damaged tooth 501 surrounded by neighbor teeth 505. The bore 508 itself may also be seen.

The 3D scan has been performed intra orally in the mouth of a patient by means of an intra oral 3D scanner.

Figure 5B:
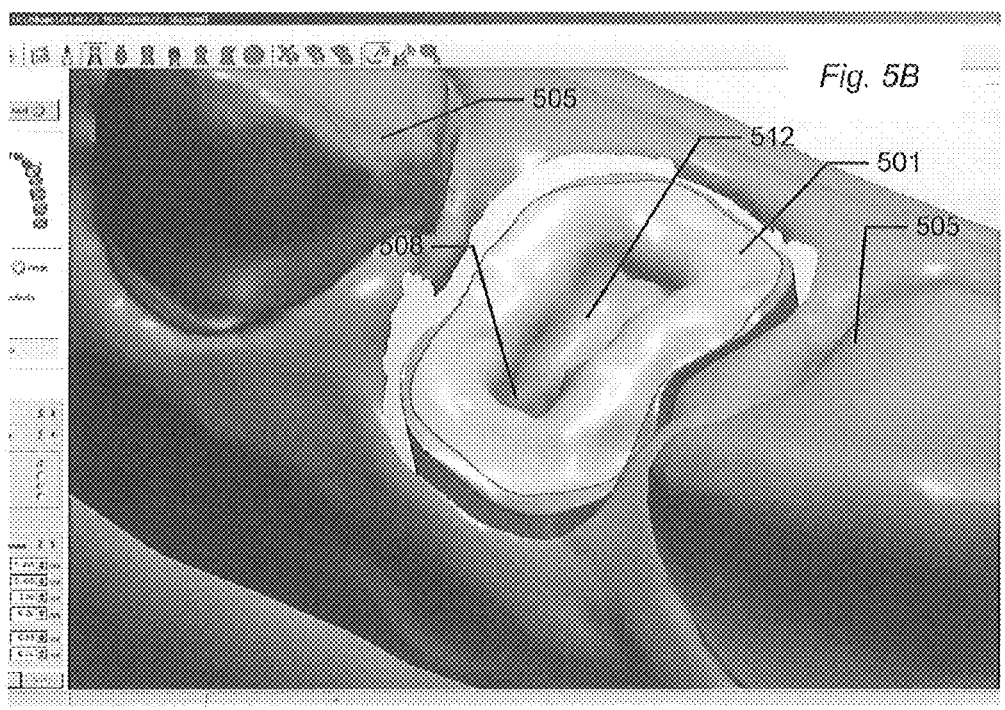

FIG. 5B shows an example of a screenshot of a 3D scan in a software program for virtual design of restorations, where the 3D scan comprises a bore opening or cavity 512 of a damaged tooth 501 surrounded by neighbor teeth 505. The bore 508 itself may also be seen.

The 3D scan may have been performed intra orally, or of a positive model of the teeth or of an impression of the teeth.

Figure 5C:
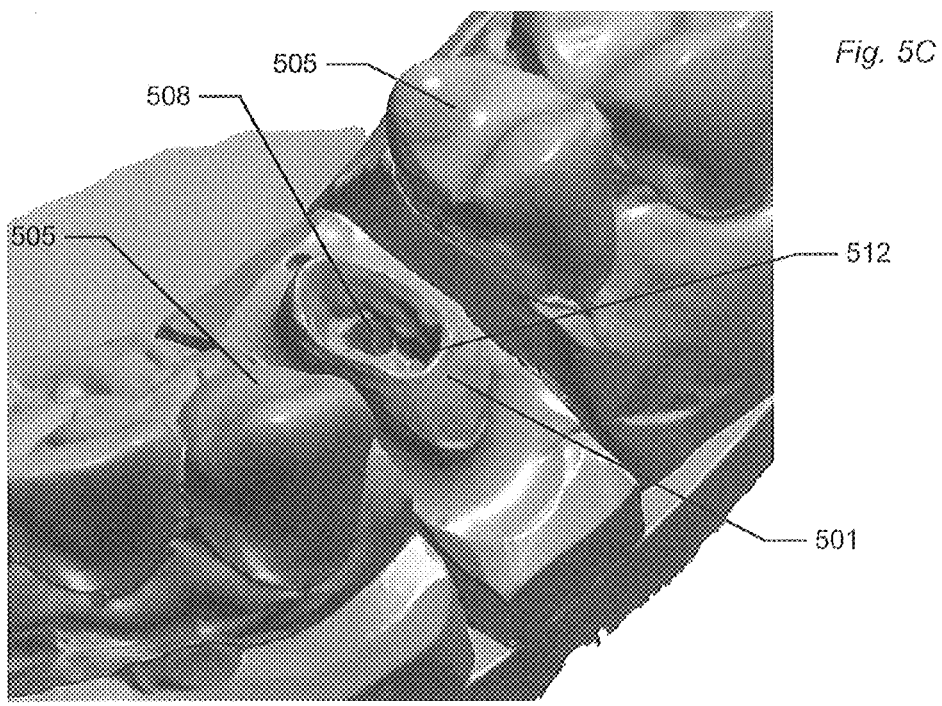

FIG. 5C shows an example of a screenshot of a 3D scan of a bore opening or cavity 512 of a damaged tooth 501 surrounded by neighbor teeth 505. The bore 508 itself may also be seen.

The 3D scan has been performed on a positive model of the teeth.

Figure 5D:
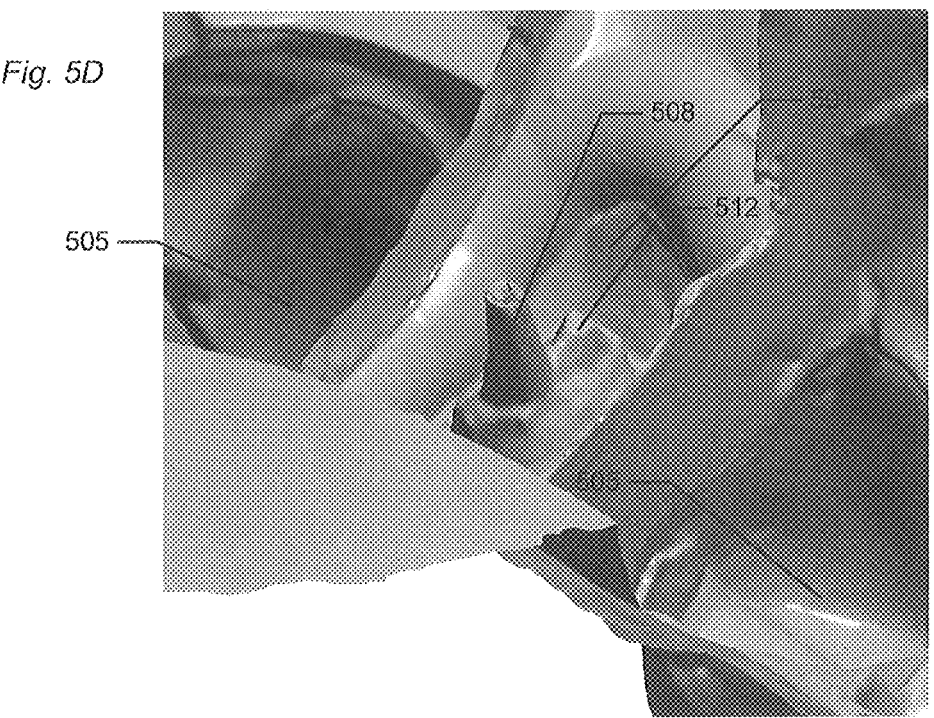

FIG. 5D shows an example of a screenshot of the 3D scan of the tooth 501 in FIG. 5C. In this screenshot the bore 508 of the damaged tooth 501 is clearly seen. The scan has been reversed compared to in FIG. 5C so that the scan of the narrow bore can be seen.

The bore opening 512 or cavity is also seen, as well as the neighbor teeth 505.

The 3D scan has been performed on a positive model of the teeth, and is the same scan as in FIG. 5C, the representation has just been inverted.

From this fig. it is clear than in some cases it is possible to scan a large part of the bore just by scanning into the bore using a 3D scanner.

FIG. 5E-5H schematically show examples of how a digital 3D shape of a post part is matched to a scan of a bore corresponding to the scan presented in FIG. 5D.

FIG. 5E show an example of a scan of a part of a bore 508 in a damaged tooth 501, where the scan corresponds to the scan of FIG. 5D. The bore is present in the root 503 of the tooth. The tooth 501 also comprises a visible tooth structure 502, which is captured in the scan, whereas the root 505 is not visible in a 3D surface scan.

FIG. 5F shows an example of a digital 3D shape 509' of a post part adapted to fit in the bore 508. The post part may the post of the post and core.

FIG. 5G shows an example where the digital 3D shape 509' of the post part is matched to the 3D scan of the tooth 501 comprising the bore 508. Matching is performed by means of corresponding surface areas of the bore 508 and of the digital 3D shape 509' of the post part.

FIG. 5H shows an example where the entire bore 508 of the tooth is represented relative to the tooth 501, and where the entire bore 508 has been derived from the matching of the digital 3D shape 509' of the post part with the part of the bore 508 obtained from the 3D scan.

Figure 6A:
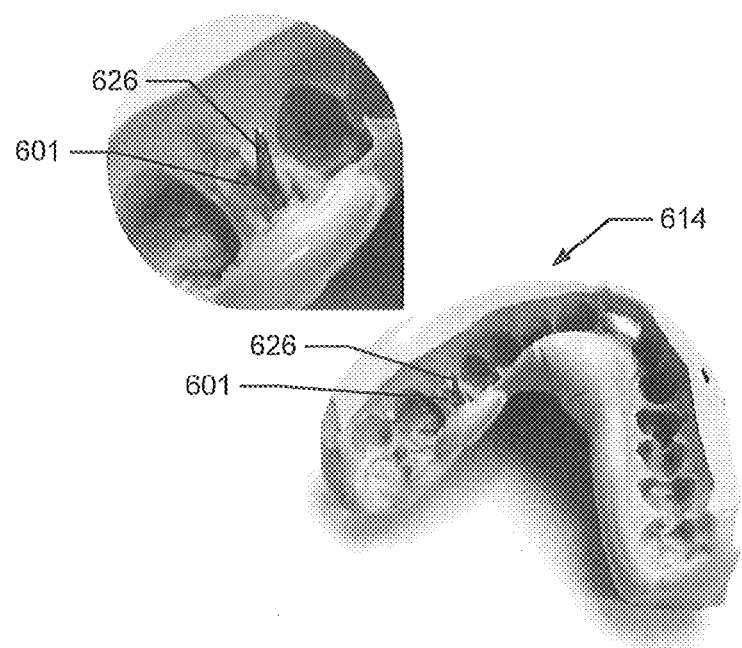
FIGS. 6A-6B show examples of an impression with a post part.
Figure 6B:
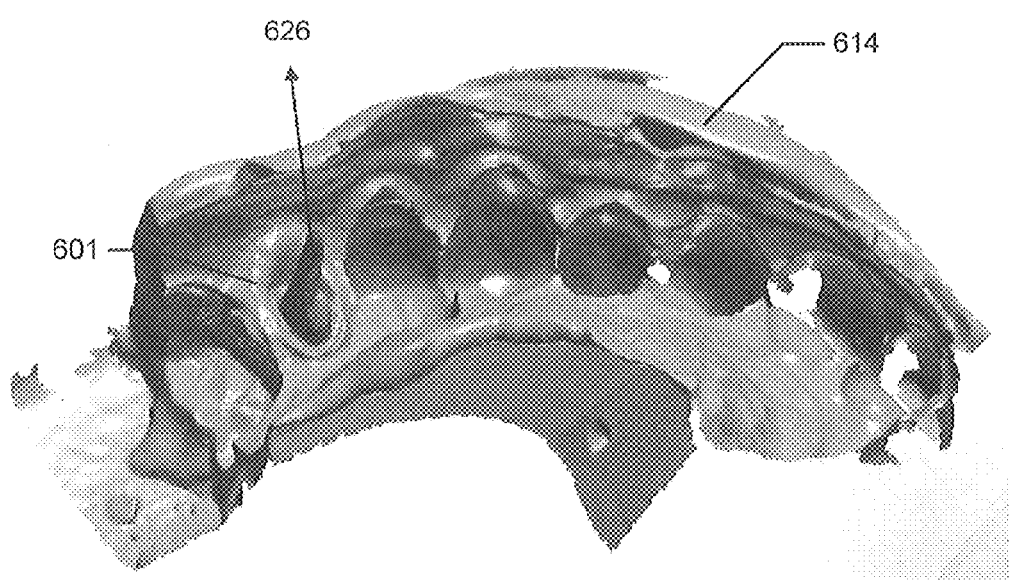

FIGS. 6A-6B show examples of an impression with a post part.

FIG. 6A shows an example of an impression 614 with a damaged tooth 601 comprising a post part 626, where the post part may be configured to be used as a scan pin corresponding to the use of the scan pin as shown in FIG. 3. The post part may have been placed in the bore of the damaged tooth before the impression material was arranged around the teeth, and when the impression was removed from the teeth, the post part in the bore may have been removed with the impression, if the post part has attached firmly to the impression.

FIG. 6B shows an example of a 3D scan of an impression 614 comprising a damaged tooth 601 with a post part 626.

By matching the 3D scan of the damaged tooth 601 comprising the post part 626 corresponding to the bore of the tooth 601 with a digital 3D shape of the post part (not shown), for example a post part as seen in FIG. 5F, the post and core can be virtually designed as outlined in FIG. 3 and FIG. 5.

FIGS. 7A-7H show examples of post and cores with multiple posts.

Figure 7A:
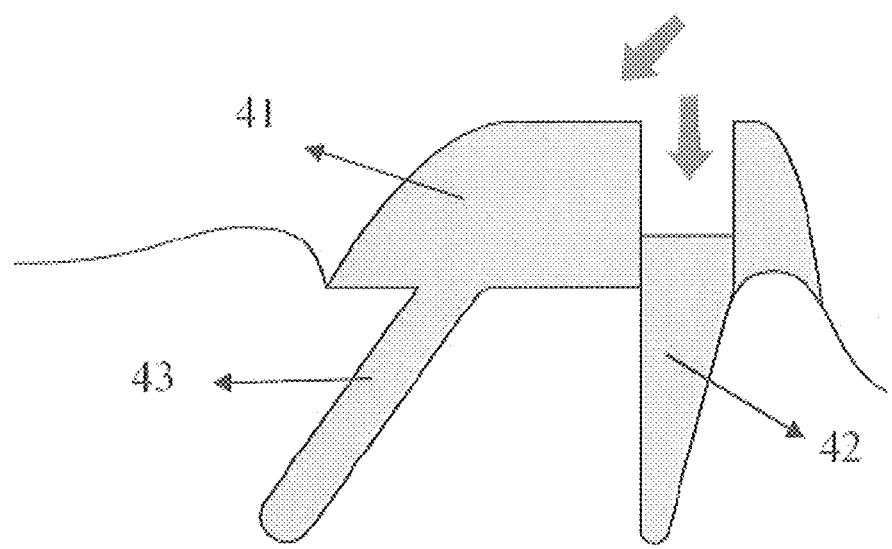

FIG. 7A shows a post and core with two posts 42, 43 and a core 41, for a tooth with multiple bores. Due to the different directions of the bores the post and core must be divided in at least two parts to provide insertion of both posts 42, 43 into the bores. The post and core model is divided in at least two parts, such as a part for each bore, providing insertion of the post and core into the bore. Insertion directions for each part and/or for each bore is provided for virtually designing the post and core with multiple posts. The insertion directions is indicated by the arrows.

FIG. 7B-7H show examples of a method for design a post and core with multiple posts.

Figure 7B:
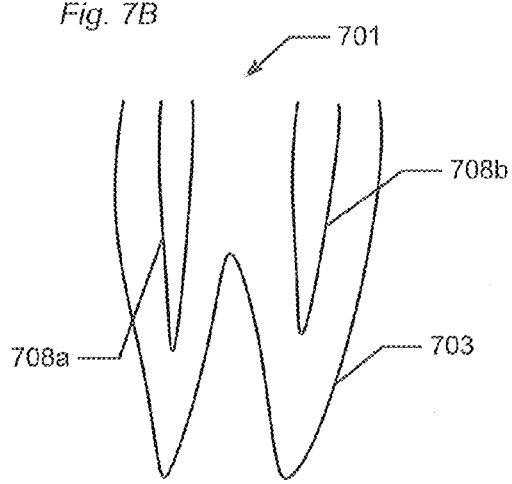

FIG. 7B shows an example a damaged tooth 701 with two root canals where a bore 708a, 708b has been prepared in each root canal of the root 703.

Figure 7C:
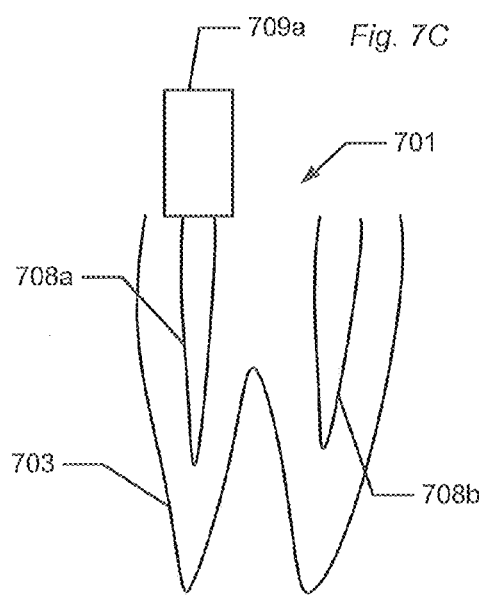

FIG. 7C shows an example where a scan pin 709a has been inserted in the bore 708a during scanning of the tooth 701. Thus the 3D scan will comprises at least part of the tooth 701 and at least part of the scan pin 709a. The insertion direction of the scan pin scan 709a in the core 708a is straight relative to the longitudinal axis of the tooth.

Figure 7D:
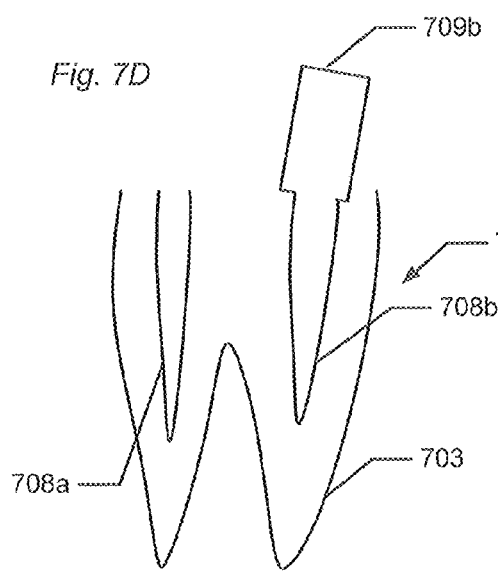

FIG. 7D shows an example where the scan pin 709a has been removed from the tooth 701, and where a scan pin 709b has been inserted in the bore 708b during scanning of the tooth 701. Thus the 3D scan will comprises at least part of the tooth 701 and at least part of the scan pin 709b.

The insertion direction of the scan pin scan 709b in the core 708b is not straight relative to the longitudinal axis of the tooth, but has an angle relative to the longitudinal axis of the tooth.

The scan pin 709a and the scan pin 709b may be the same scan pin or two different scan pins.

Figure 7E:
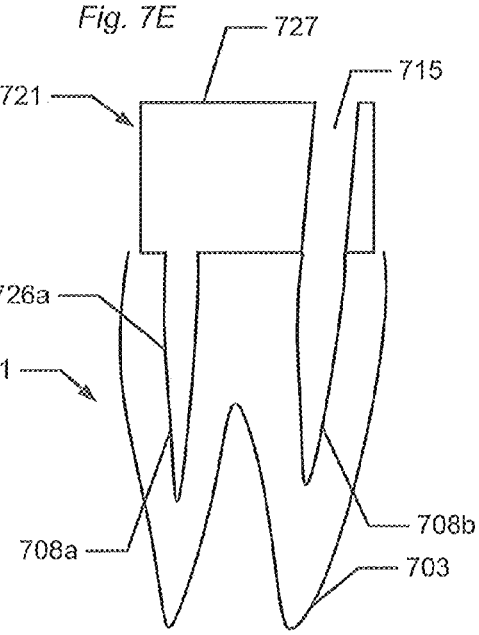

FIG. 7E shows an example where the first part of the post and core 721 comprising a post 726a in the bore 708a and a core 727 connected with the post 726a is attached in the tooth. The core 727 comprises a through-hole 715 to the bore 708b.

FIG. 7F shows an example where a clavette or second part 716 of the post and core 721 is arranged in the first part of the post and core 721 in the through-hole 715 of the core 727 and in the bore 708b. The clavette or second part 716 comprises a post 726b in the bore 708b. The clavette of second part 716 is longer than the total length of the bore 708b and the through-hole 715 in the core for facilitating insertion of it and it comprises a notch 717 level with the upper part of the core 727. When the clavette or second part 716 has been attached in the post and core 721, the excess part of the clavette or second part 716 can be removed, such as cut of, snapped of etc.

FIG. 7G shows an example where the excess part of the clavette or second part 716 has been removed, such as cut of, snapped of etc., and the clavette or second part 716 is now level or flush with the core 727.

FIG. 7H shows an example where the entire restoration for the damaged tooth 701 is virtually designed. Around the core 727 is a coping 722 and crown 723 virtually designed. The order or sequence of which the different parts of the restoration are virtually designed may be different than shown in the figures.

FIGS. 8A-8F show examples of different digital means and software tools for performing and facilitating the matching and representing the 3D scan of the tooth and the digital 3D shape.

Figure 8A:
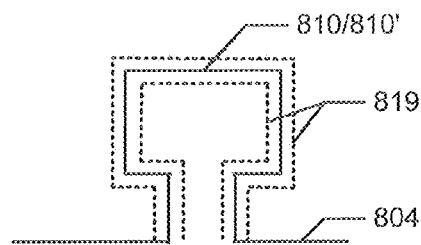
FIGS. 8A-8F show examples of different digital means and software tools for performing and facilitating the matching and representing the 3D scan of the tooth and the digital 3D shape.

FIG. 8A shows an example of marking the outer part of a scan pin for the purpose of deleting it. The vicinity of the outer part 810 of the scan pin is marked in an area 819 surrounding it down to the gingival 804. The vicinity may be for example about 20 micrometer from the surface of the scan pin. The area 819 around the outer part 810 of the scan pin to be deleted is marked with dotted lines. The outer part 810 of the scan pin may be deleted in the 3D scan, that is 810, and/or in the digital 3D shape, that is 810', for providing a better visualization and representation of the post part relative to the tooth.

Figure 8B:

FIG. 8B shows an example where the outer part 810 of the scan pin has been deleted, for example based on the procedure of FIG. 8A, leaving a hole 820 in the surface of the gingival on the 3D scan.

Figure 8C:
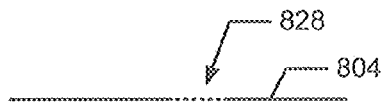

FIG. 8C shows an example where the hole in the surface as seen in FIG. 8B has been virtually hole closed 828, indicated by the dotted lines, such that the surface of the gingival 804 is not closed.

Figure 8D:
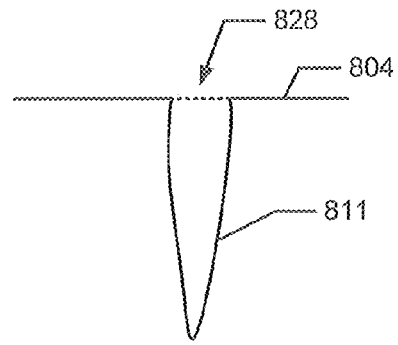

FIG. 8D shows an example where a post part 826 from a digital 3D shape has been added to the 3D scan, such that the post part 826 is level with the gingival 804 in the area where hole closing 828 has been performed, as seen in FIG. 8C.

Figure 8E:
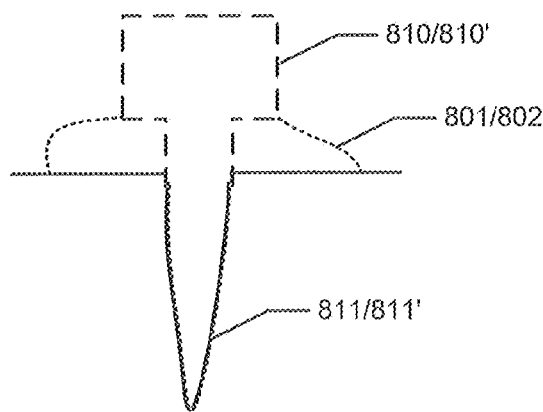

FIG. 8E shows an example where the entire scan pin 809 comprising an outer part 810/810' and an inner part or post part 811/811' is shown relative to the 3D scan of the tooth 801 represented by its remaining tooth structure 802. The scan pin may be from a digital 3D shape and/or from a 3D scan.

Figure 8F:
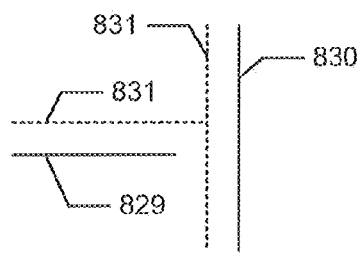

FIG. 8F shows an example of offsetting surfaces for providing transition between different surfaces. The surface 829 of the 3D scan and the surface 830 of the 3D digital shape is offsetted 831 to obtain a closed surface after deletion of for example the outer part of the scan pin from the 3D scan.

FIGS. 9A-9F show how a combined surface scan is provided which can be used as a basis for designing a virtual model of a post and core with multiple posts.

Figure 9A:
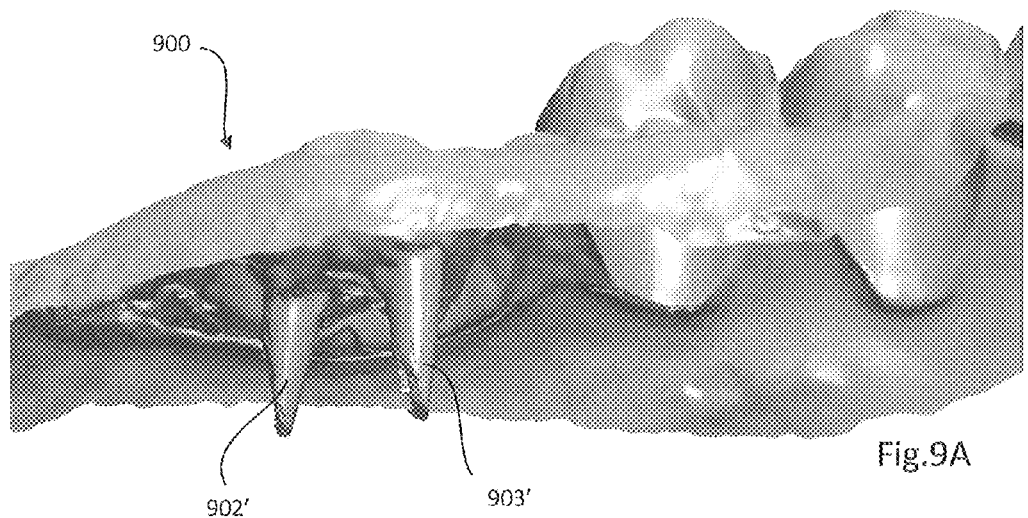
FIGS. 9A-9G show an example of how to provide a highly detailed representation of the bores of a damaged tooth.
Figure 9B:
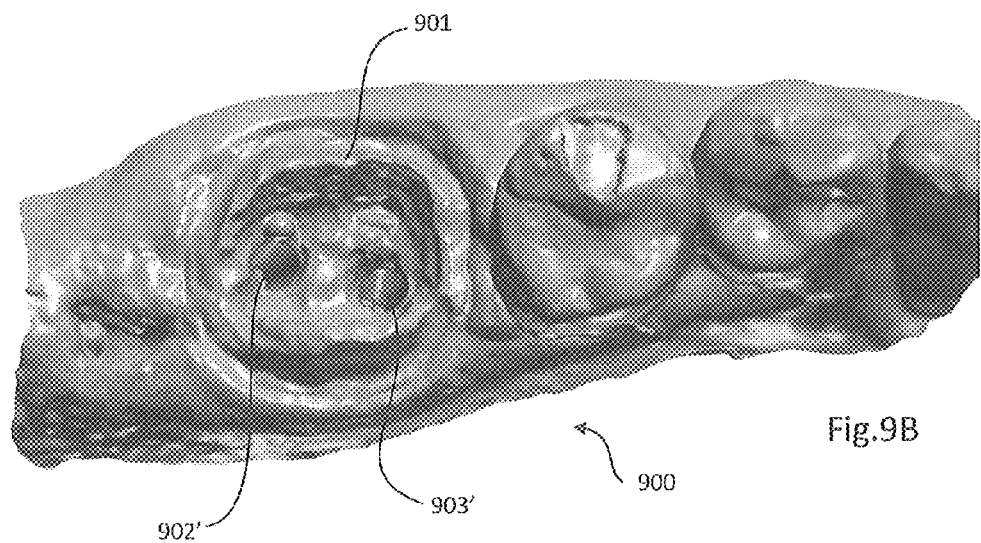

FIGS. 9A and 9B show a first surface scan 900 shown in two different perspective views. The first surface scan comprises a scan of a dental preparation 901 of a molar with two virtual partial representations 902', 903' of bores created by the dentist in the roots of the molar.

The first surface scan 900 is created by scanning a gypsum model with a TRIOS scanner, which is an intra-oral scanner manufactured by 3Shape A/S, Denmark. The first surface scan could also have been provided by scanning the patient directly in the mouth using the TRIOS.

However, in a scan as the first surface scan 900 it is preferred to obtain the complete virtual representation 902, 903 of the bores as will be described.

After the first surface scan 900 is obtained a second surface scan (not shown) of the same area is obtained. When this scan is obtained first and second scan posts are placed in the respective bores. Thus, the second surface scan comprises the virtual representations of the visible parts 904, 905 of the first and second scan posts. The scan posts used have posts with identical size and shape as the drill used by the dentist when he created the bores.

Figure 9C:
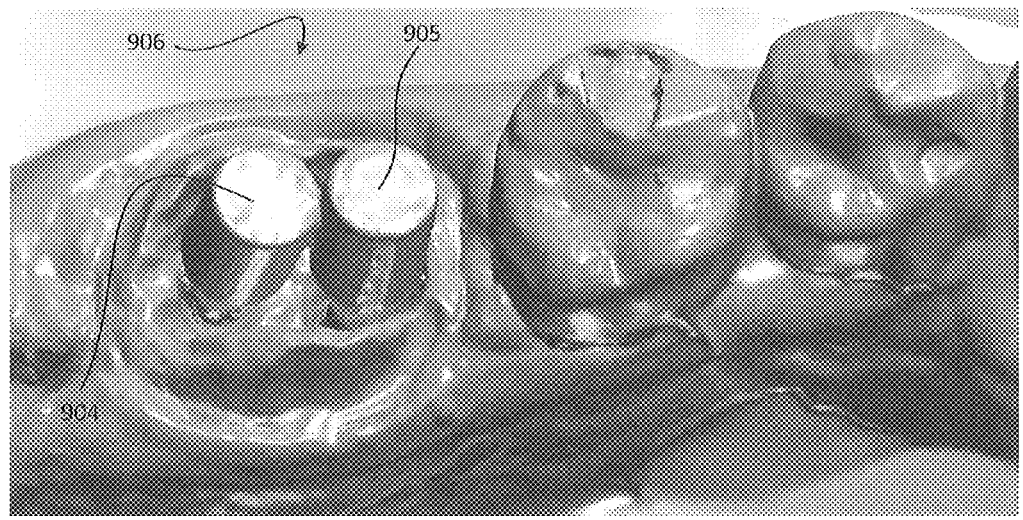
Figure 9D:
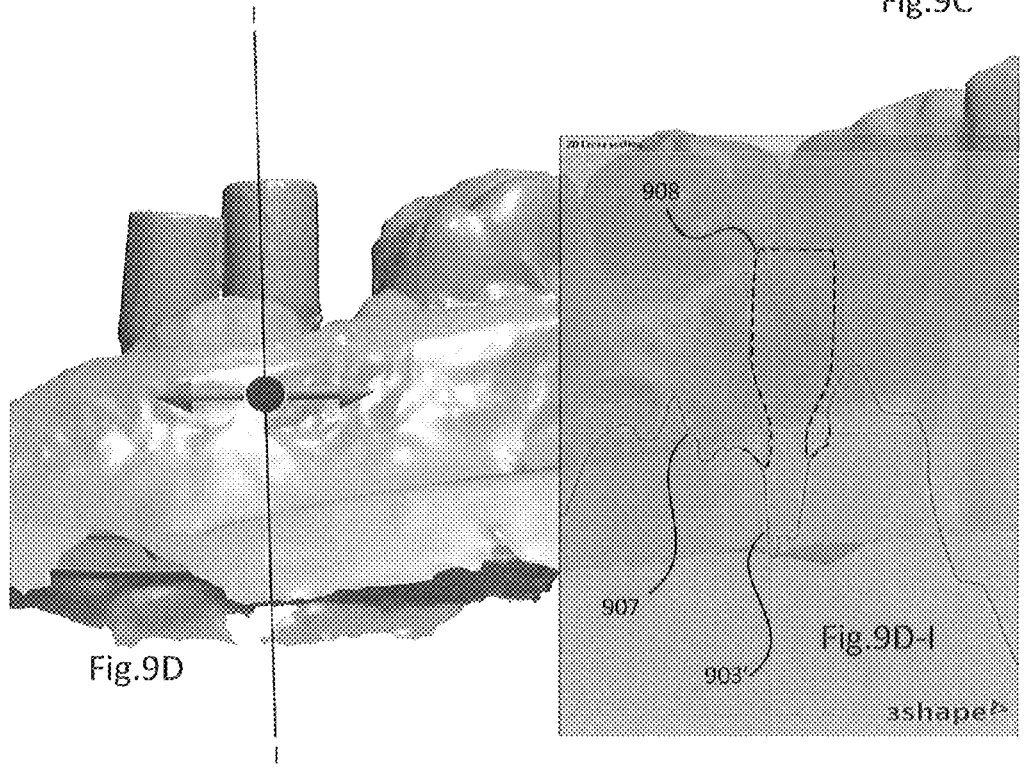

However, the second surface scan will not be complete since there will be areas of the dental preparation 901 which will be occluded by the scan pins. However, such information is present in the first surface scan. Thus, by combining the first and the second surface scan into a third surface scan 906 as seen in FIG. 9C information on the dental preparation 901 from the first surface scan can be combined with information on the first and second scan pin from the second surface scan.

In FIG. 9D-I there is shown a cross section of the third surface scan 906 along line I-I FIG. 9D-I. The cross section shows the first surface scan along the solid line 907 and part of the second surface scan comprising the scan pin along the broken line 908 in alignment with each other.

In the current embodiment it should be understood that the second surface scan corresponds to first 3D scan, the first surface scan corresponds to the second 3D scan and the third surface scan corresponds to the 3D image which is a combination of the first and second 3D scan as described herein.

Figure 9E:
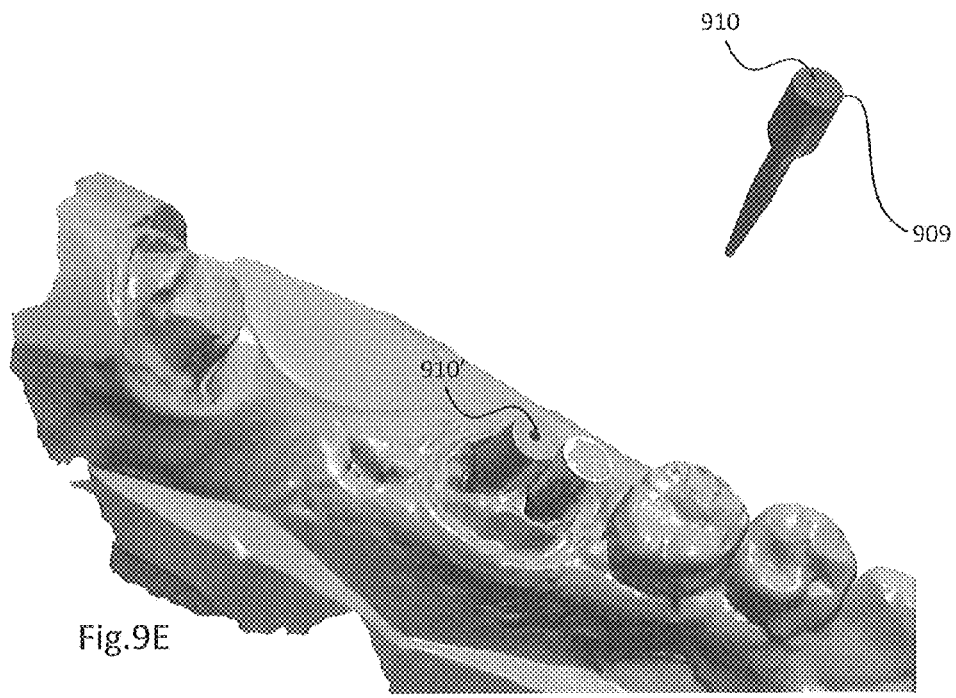

When the third surface scan 906 has been provided a CAD model of the scan pin 909 is aligned to the visible parts of the scanned scan pins 904,905 as shown in FIG. 9E. The alignment is done by identifying identical surfaces on the CAD model of the scan pin and on the third surface scan 906. Alignment algorithms known in the art can then be used to align the surfaces together with minimal deviation. In FIG. 9E the surface identified on the CAD model and the corresponding surface on the third surface scan is marked with dots 910, 910' respectively.

Figure 9F:
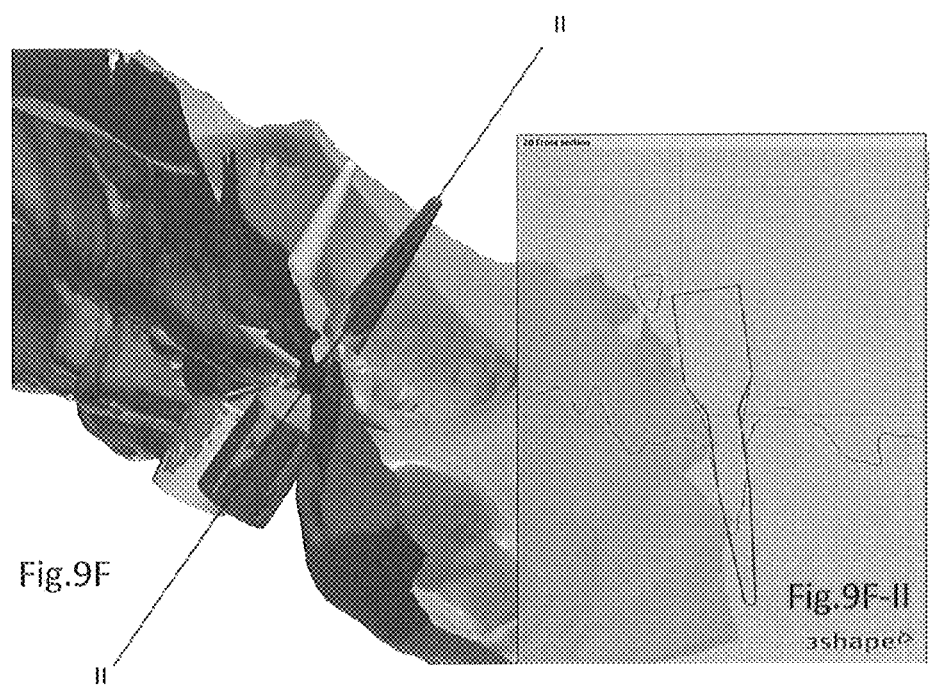

FIG. 9F-II shows in section along line II-II in FIG. 9F how the CAD file of the scan post have been aligned with the third surface scan.

Figure 9G:
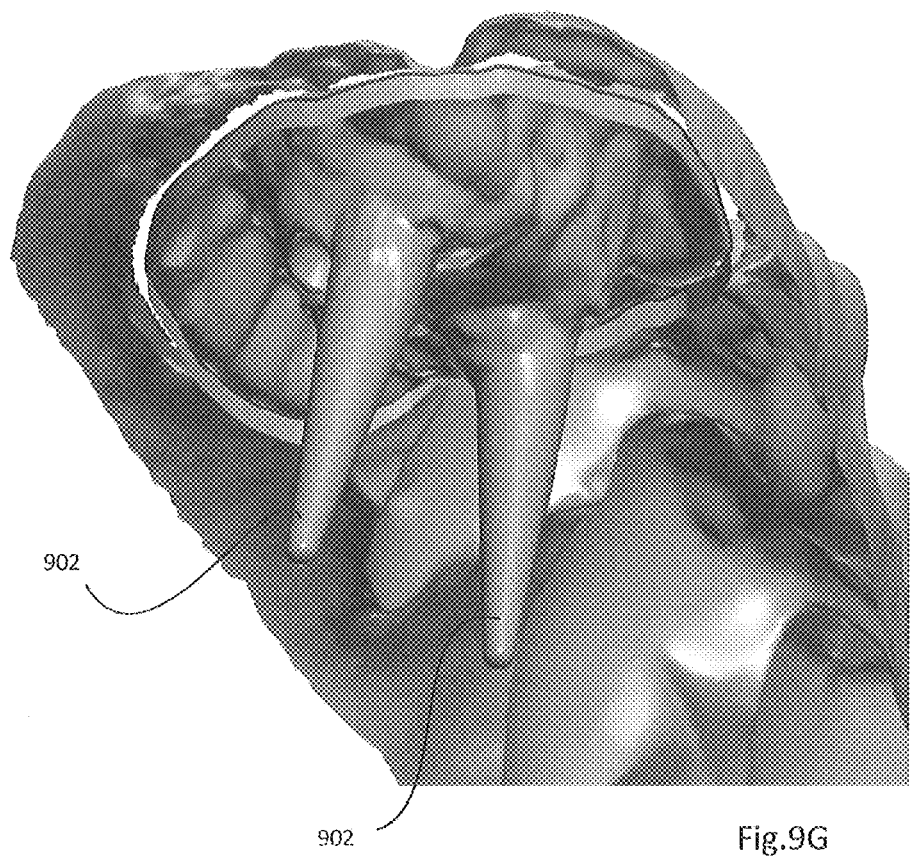

When the CAD file has been aligned with the scanned scan pins 904, 905 of the third surface scan the posts of the scan pins is combined with the third surface scan 906 thereby creating a full representation of each of the bores 902, 903 as shown in FIG. 9G.

When the a complete surface scan containing all the information about the dental preparation 901; 1001 a virtual model of the post and core restoration can be designed as will be described with reference to FIGS. 10A-10E. FIGS. 10A-10E show a case where a virtual model of a restoration 1005 based on a post and core 1006 is designed. The post and core model is a single post model prepared to fit into the dental preparation 1001 including the root bore 1007.

The user starts the design by marking the margin line 1002 of the preparation. This outer or preparation margin line 1002 indicates the edge of where the dentist has prepared the tooth. The preparation margin line is used as a boundary for designing the restoration as will also be described in the following and which is well known to the person skilled in the art.

Besides the preparation margin line 1002 a core margin line 1003 is also marked. The core margin line 1003 defines a design boundary of the core on the virtual model of the post and core as will be described. The core margin line 1003 does not extend beyond the preparation margin line but extend within the boundaries of the preparation margin line. In some cases the core margin line may coincide with the preparation margin line as can be seen in one area 1004 of the designs of the margin lines in FIG. 10A.

When preparation margin line 1002 and the core margin line 1003 has been marked an insertion direction for the restoration 1008 and an insertion direction for the post and core 1009 is determined. As can be seen in the current case the restoration insertion direction 1008 and the post and core insertion direction coincide. However, in many cases they may differ since the post and core model have to consider the root bore 1007 when determining the post and core insertion direction, while the restoration 1005 have to considered other obstacles such as neighboring teeth.

Figure 10A:
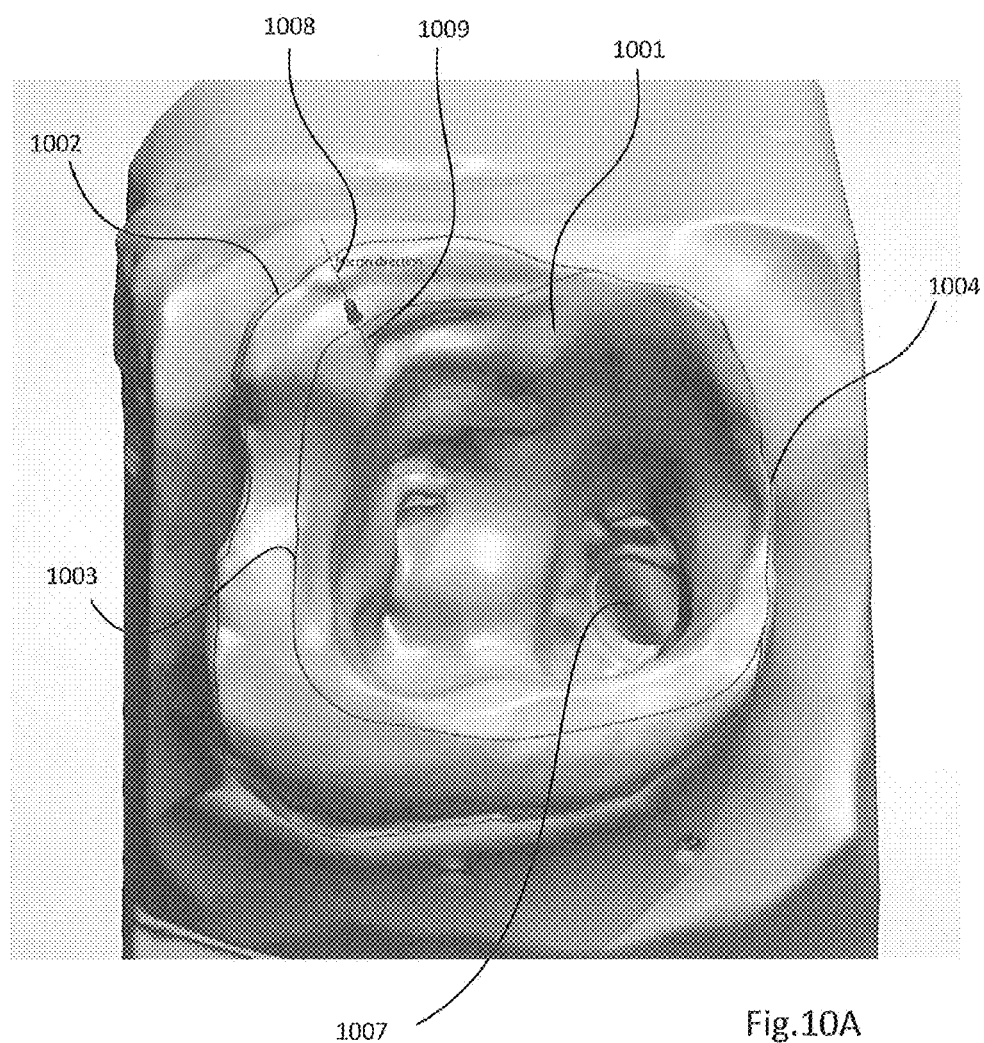
FIGS. 10A-10E show an example on how to design a virtual model of a post and core.
Figure 10B:
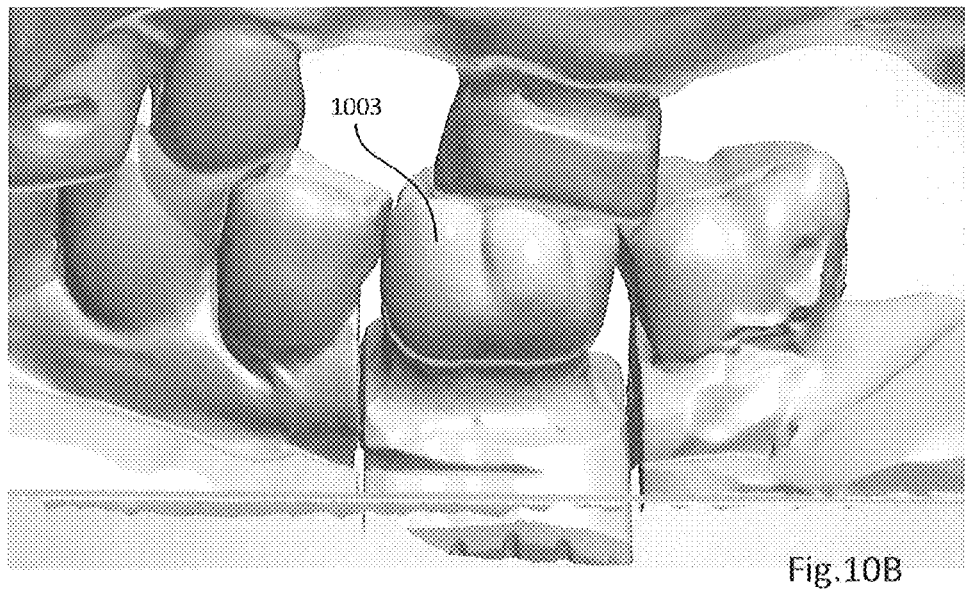

After the margin lines and the insertion directions have been determined the restoration may be designed. In the current case the restoration is a crown 1005 which is designed as shown in FIG. 10B.

The crown 1005 is anatomically designed to have a nice look, fit correctly between neighboring teeth and provided proper occlusal contact with antagonist teeth.

Figure 10C:
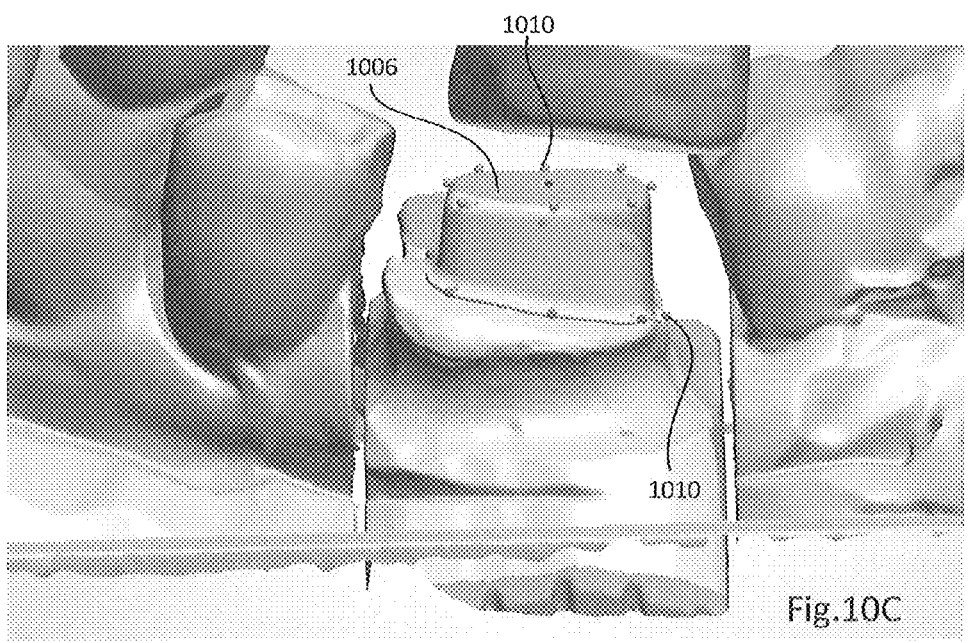
Figure 10D:
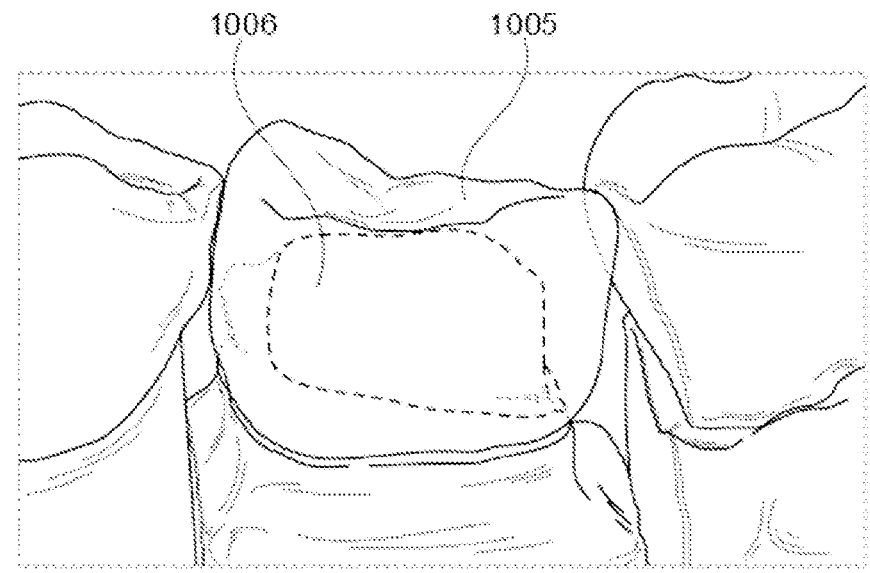

After the anatomy of the crown has been designed the post and core is designed as shown in FIG. 10C. The post and core is defined by the surface of the dental preparation 1001 defined by the post and core margin line 1009 and a surface cap extending from the post and core margin line. The surface cap corresponds to the visible portion of the post and core model 1006 shown in FIG. 10C.

For allowing the user to manipulate the design control point in the form of spheres 1010 are provided on the model of the post and core. The spheres can be manipulated so that the design of the visible part of the post and core may be altered.

Figure 11A:
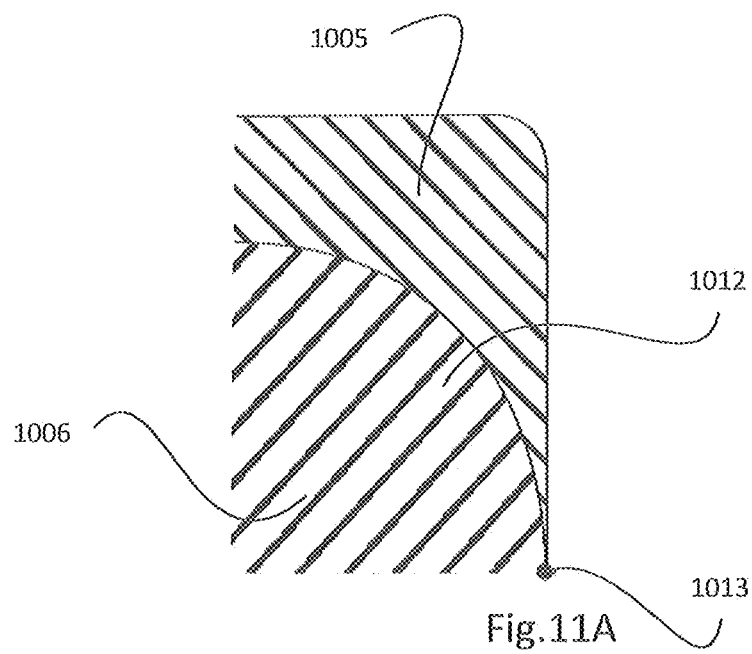
FIGS. 11A-11B show an example on how to provide a shoulder on the core of a post and core model.
Figure 11B:
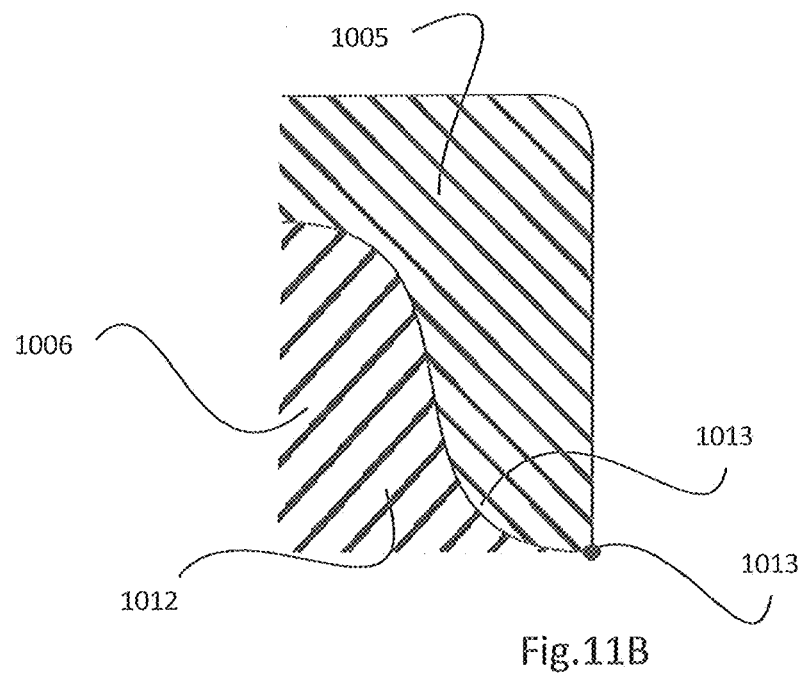
Figure 12A:
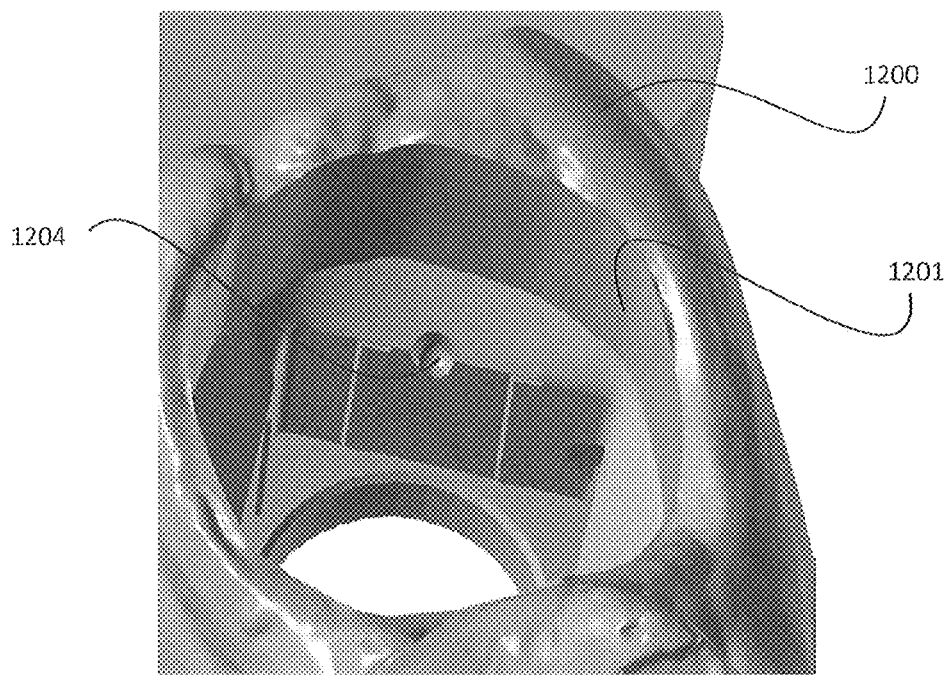
FIGS. 12A-12B show an example of how to provide a working model suitable for post and core restorations.
Figure 12B:
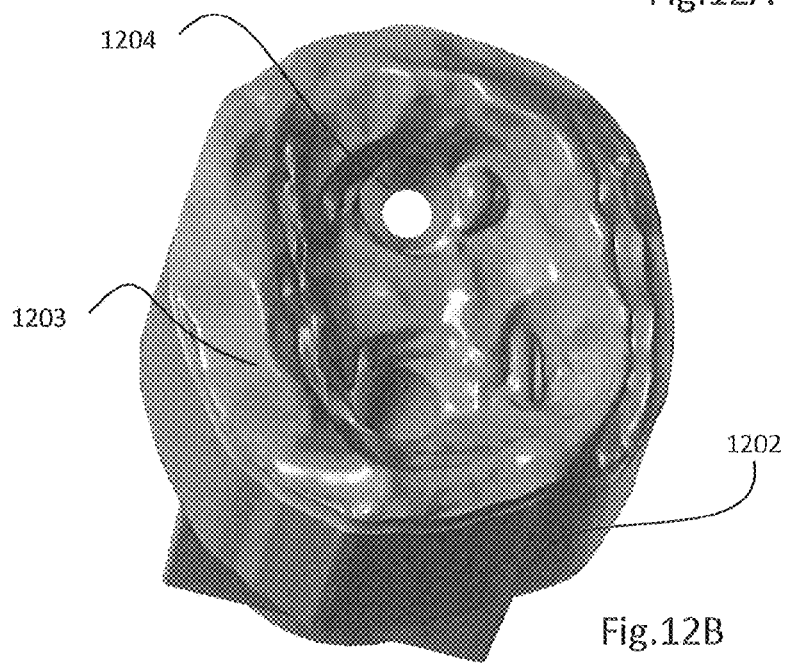

One particular feature which advantageously be provided by using the control points is a shoulder on the core. In the case of coinciding margin lines 1004 which is the case in the current case there is a risk that the material of the crown become too thin in area close to the margin lines, which us shown in FIG. 10A. However, by providing a shoulder, as shown in FIG. 11B, in the shape of a rounding, bevel or chamfer on the core model at the margin lines. This drastically increases the thickness of the crown in that area and thus ensures that the minimal thickness of the material of the crown 1005 is maintained.

The crown 1005 and post and core model 1006 can then be finalized and prepared for production. Such finalization may for example include providing a cement gap between the crown and the core and removing undercuts from e.g. the post so that it may be inserted into the prepared root bore of the patient.

Figure 10E:
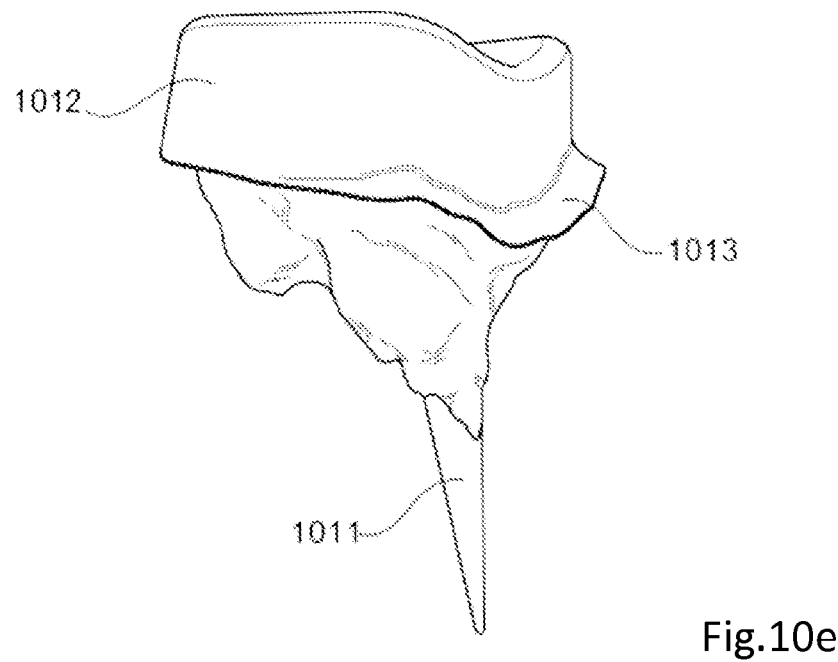

The final model of the post and core 1006 can be seen in FIG. 10E. For example, the post and core has a post part 1011*a* core part 1012 and a shoulder 1013.

In some cases the dental technician or other person working on the restoration may want to work on a physical model. Such physical models are generally known and can for example be produced by printing a virtual dental model representing the preparation site and the area surrounding it, e.g. the neighboring teeth. Typically a first model 1200 is produced which represents the surrounding area. The first model is provided with a slot 1201 into which a die 1202 can be placed. The die is a model of the dental preparation 1203. In case there are multiple dental preparations then multiple slots are formed in the first model for each preparation for which a restoration is to be prepared and a corresponding die for each slot is also produced.

As mentioned it is common to produce such models for many types of restorations and combinations thereof. However, such known models are not always suitable for post and core restorations.

The die 1202 has to fit into the slot 1201 and at the same time it has to fit between neighboring representations of teeth on the model. With post and core models the post part or what in the model and represent the root bore will in some cases extend below neighboring teeth or structures on the model. Thus to limitations has to be considered, first that the die has to fit into the slot, and secondly that it should be possible to place a post and core model in the die 1202.

In order to make this possible the bore representation 1204 which extends below neighboring structure is extended from the die 1202 and into the model. This advantageously allows for post and core models which have posts that extend below adjacent structures to be inserted in the physical model.

Figure 13:
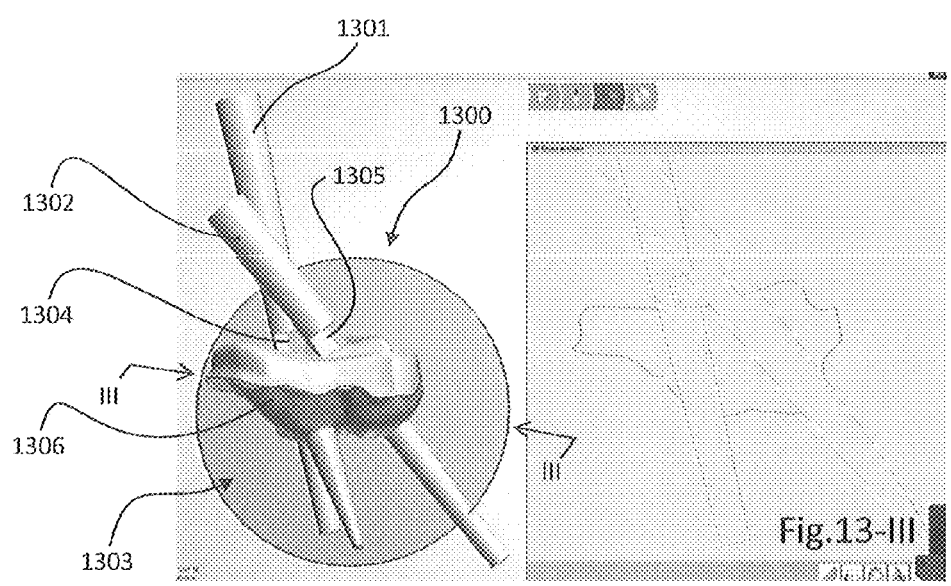
FIG. 13 shows an example on how to ensure that clavettes are designed so as to fit in a multiple cost and post model with high accuracy.

In one embodiment as illustrated in FIGS. 13 and 13 III, which is a sectional view of FIG. 13 along the plane III-III defined by the circle 1300.

As described earlier clavettes 1301 and 1302 are used in a post and core 1303 having multiple posts to form the additional posts.

Advantageously notches 1304 and 1305 are provided during design of the post and core model. The notches indicates how far the clavette should be inserted into the core 1306 of the post and core model.

Thus, when the parts are manufactured the dentist knows exactly how far into the bore the clavettes should be placed and a clear indication of where to correctly cut the clavettes are provided.

FIGS. 14A-14D show one embodiment of a scan pin 1400 with dimensions in millimeters.

FIG. 14A shows the scan pin in a side view, where it is rotational symmetrical around the axis A-A. The scan pin has a scan head 1401 from which a scan post 1402 extends. The end of the scan post opposite the scan head is formed with a tapering portion 1403 which has a shape that matches a typical dental drill.

FIG. 14B shows the scan pin in a top view, i.e. seen from the scan head.

FIG. 14C shows the scan pin in a bottom view, i.e. seen from the tapering portion.

FIG. 14D shows the scan pin in a perspective view.

The scan pin is preferably made from a relative rigid polymer material, such as polyether ether ketone (PEEK). It should of course understood that the choice of material is not necessarily dependent on the shape and dimensions of the scan pin.

The material should also preferably be radiopaque in order to be able to locate the scan pin in case the patient swallows it.

FIGS. 15A-15D show another embodiment of a scan pin 1500 with dimensions in millimeters. Similar to the scan pin 1400 described above it has a scan head 1503, a scan post 1502 extending therefrom, and a tapering portion 1503 formed on the scan post.

However, the dimensions are slightly different, e.g. the diameter of the scan post differs slightly and the tapering portion tapers with a different angle and thus its shape corresponds to that of a different dental drill.

As can be seen in FIGS. 14A-15D the dimensions may vary depending on the shape of the drill that the dentist has used, which again may depend on the tooth, the root shape and other factors.

However, at least two parameters are of particular interest when designing the scan pins as illustrated in FIGS. 14A-15D. These are the diameter $d_1$ of the scan post 1402; 1502 at its thickest and the tapering angle $\alpha_1$ of the tapering portion 1403; 1503.

The diameter $d_1$ of the scan post is preferably between 1 and 2 millimeters. In particular between 1.2 and 1.8 millimeters, such as 1.5 millimeters or 1.7 millimeters.

The tapering angle $\alpha_1$ of the tapering portion is preferably between 5° and 10°. In particular between 6° and 8°.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

EMBODIMENTS

1. A method of virtually designing a post and core restoration adapted for attachment in a damaged tooth of a patient, where the damaged tooth comprises a bore for receiving the post of the post and core, wherein the method comprises:
   obtaining a 3D image comprising a first 3D scan comprising at least a part of the damaged tooth;
   providing a digital 3D shape adapted to fit the bore of the damaged tooth;
   virtually matching the first 3D scan of the tooth and the digital 3D shape, where the matching comprises matching a surface region in the first 3D scan of the tooth with a corresponding surface region of the digital 3D shape, such that at least part digital 3D shape is represented relative to the first 3D scan of the tooth;
   virtually designing the post and core restoration based on the representation of the digital 3D shape relative to the first 3D scan of the tooth.

2. A method according to embodiment 1, further comprising that the digital 3D shape is at least a part of a surface representation adapted for matching at least a part of the bore of the damaged tooth.

3. A method according to embodiment 1 or 2, further comprising that the digital 3D shape is at least a part of a component adapted for fitting to the damaged tooth, where the component comprises at least a post part adapted for fitting in the bore of the damaged tooth.

4. A method of virtually designing a post and core restoration adapted for attachment in a damaged tooth of a patient, wherein the method comprises:
   obtaining a 3D image comprising a first 3D scan comprising at least part of the damaged tooth;
   providing a digital 3D shape of a post corresponding to the post of the post and core;
   virtually matching the first 3D scan of the tooth and the digital 3D shape of the post, where the matching comprises matching a surface region in the first 3D scan of the tooth with a corresponding surface region of the digital 3D shape of the post;
   virtually designing the post and core based on the virtual matching of the first 3D scan of the tooth and the digital 3D shape of the post.

5. A method of virtually designing a post and core restoration adapted for attachment in a damaged tooth of a patient, wherein the method comprises:
   obtaining a 3D image comprising a first 3D scan of at least part of the patient's set of teeth comprising the damaged tooth, where a scan pin comprising an outer part and an inner part is arranged in the tooth during the 3D scanning, such that the outer part of the scan pin is located at least partly outside the tooth, and the inner part of the scan pin is located at least partly in the tooth, where the inner part of the scan pin corresponds to the post of the post and core, and where the first 3D scan comprises the tooth and at least a part of the scan pin;

providing a digital 3D shape of the scan pin comprising the outer part and the inner part of the scan pin;

virtually matching the first 3D scan with the digital 3D shape of the scan pin, where the matching comprises matching the at least part of the scan pin of the first 3D scan with the at least part of the scan pin of the digital 3D shape, such that the inner part of the scan pin of the digital 3D shape is represented relative to the tooth in the first 3D scan;

virtually designing the post and core based on the representation of the inner part of the scan pin relative to the tooth in the first 3D scan.

6. A method of virtually designing a post and core restoration adapted for attachment in a damaged tooth of a patient, wherein the method comprises:

obtaining a 3D image comprising a first 3D scan of at least part of the patient's set of teeth comprising the damaged tooth, where a scan pin comprising an outer part and an inner part is arranged in the tooth bore during the 3D scanning, such that the outer part of the scan pin is located at least partly outside the tooth, and the inner part of the scan pin is located at least partly in the tooth, where the inner part of the scan pin corresponds to the post of the post and core, and where the first 3D scan comprises the tooth and at least a part of the scan pin;

providing a digital 3D shape of the scan pin comprising the outer part and the inner part of the scan pin;

virtually matching the first 3D scan with the digital 3D shape of the scan pin, where the matching comprises matching the outer part of the scan pin of the first 3D scan with the outer part of the scan pin of the digital 3D shape, such that the inner part of the scan pin of the digital 3D shape is represented relative to the tooth in the first 3D scan;

virtually designing the post and core based on the representation of the inner part of the scan pin relative to the tooth in the first 3D scan.

7. The method according to any one or more of the preceding embodiments, wherein the digital 3D shape of the component is a digital 3D shape of a post corresponding to the post of the post and core.

8. The method according to any one or more of the preceding embodiments, wherein the digital 3D shape of the component is a digital 3D shape of a scan pin comprising an inner part and an outer part, where the outer part of the scan pin is located at least partly outside the tooth, and the inner part of the scan pin is located at least partly in the tooth, where the inner part of the scan pin corresponds to the post part.

9. The method according to any one or more of the preceding embodiments, wherein the method further comprises: virtually deleting the outer part of the scan pin from the first 3D scan after the matching.

10. The method according to any one or more of the preceding embodiments, wherein virtually deleting the outer part of the scan pin from the first 3D scan comprises deleting points in an area surrounding the shape of the outer part of the digital 3D shape.

11. The method according to any one or more of the preceding embodiments, wherein the method further comprises: performing virtual hole closing of the missing surface which arise after deletion of the outer part of the scan pin from the first 3D scan.

12. The method according to any one or more of the preceding embodiments, wherein the method further comprises: offsetting the surface of the 3D scan and/or the surface of the 3D digital shape to obtain a closed surface after deletion of the outer part of the scan pin.

13. The method according to any one or more of the preceding embodiments, wherein representing the inner part of the scan pin of the digital 3D shape relative to the tooth in the first 3D scan comprises virtually providing the inner part of the scan pin from the 3D digital shape to the first 3D scan.

14. The method according to any one or more of the preceding embodiments, wherein virtually providing the inner part of the scan pin from the 3D digital shape to the first 3D scan comprises performing a Boolean subtraction of the inner part of the scan pin from the first 3D scan.

15. The method according to any one or more of the preceding embodiments, wherein the 3D image further comprises a second 3D scan of at least part of the patient's set of teeth comprising the damaged tooth, where no scan pin is arranged in the tooth bore during the 3D scanning, and where the second 3D scan comprises at least part of a cavity of the tooth adapted for attachment of the post and core in the tooth.

16. The method according to any one or more of the preceding embodiments, wherein the 3D image is a virtual combination of the first 3D scan comprising the tooth and the component with the second 3D scan only comprising the tooth.

17. The method according to any one or more of the preceding embodiments, wherein the method further comprises representing the scan pin comprising the outer part and the inner part relative to the damaged tooth in the second 3D scan.

18. The method according to any one or more of the preceding embodiments, wherein the method further comprises: providing a transition between the surface of the tooth cavity from the second 3D scan and the surface of the scan pin from the digital 3D shape.

19. The method according to any one or more of the preceding embodiments, wherein providing the transition between the surface of the tooth cavity from the second 3D scan and the surface of the scan pin from the digital 3D shape comprises performing hole closing of surface areas and/or offsetting of surfaces.

20. The method according to any one or more of the preceding embodiments, wherein the post and core restoration adapted for attachment in a damaged tooth comprises at least two posts, whereby the damaged tooth comprises at least two bores, and where a first post of the at least two posts is adapted for attachment in a first bore of the at least two bores, and where a second post of the at least two posts is adapted to attachment in a second bore of the at least two bores.

21. The method according to any one or more of the preceding embodiments, wherein the method comprises obtaining a third 3D scan of at least part of the patient's set of teeth comprising the damaged tooth, where a first scan pin comprising an outer part and an inner part is arranged in the first bore during the 3D scanning, such that the outer part of the first scan pin is located at least partly outside the tooth, and the inner part of the first scan pin is located at least partly in the tooth, where the inner part of the first scan pin corresponds to the first post of the post and core, and where the third 3D scan comprises the tooth and at least part of the outer part of the first scan pin.

22. The method according to any one or more of the preceding embodiments, wherein the method comprises obtaining at fourth 3D scan of at least part of the patient's set of teeth comprising the damaged tooth, where a second scan pin comprising an outer part and an inner part is arranged in the second bore during the 3D scanning, such that the outer part of the second scan pin is located at least partly outside the tooth, and the inner part of the second scan pin is located at least partly in the tooth, where the inner part of the second scan pin corresponds to the second post of the post and core, and where the fourth 3D scan comprises the tooth and at least part of the outer part of the second scan pin.

23. The method according to any one or more of the preceding embodiments, wherein the method comprises combining the third 3D scan and the fourth 3D scan of the tooth and the outer part of each of the scan pins for designing the post and core comprising at least two posts.

24. The method according to any one or more of the preceding embodiments, wherein the method comprises virtually designing the post and core comprising at least two posts such that the at least two posts physically are configured to be inserted in the tooth.

25. The method according to any one or more of the preceding embodiments, wherein virtually designing the post and core comprising at least two posts comprises:
designing the core and the first post as one piece;
designing the second post as a separate piece; and
designing a through-hole in the core for insertion of the second post in the tooth through the core.

26. The method according to any one or more of the preceding embodiments, wherein the method comprises virtually designing the second post to have a length longer than its final length for fitting in it's bore and through the core for facilitating the insertion of the second post.

27. The method according to any one or more of the preceding embodiments, wherein the method comprises virtually designing an indentation on the second post at the position where the second post protrudes from the core, when the second post is inserted in the second bore, and where the excess part of the second post protruding from the core is adapted to be removed at the indentation.

28. The method according to any one or more of the preceding embodiments, wherein a visible marker present on the scan pin uniquely identifies the shape of the post of the post and core.

29. The method according to any one or more of the preceding embodiments, wherein the first 3D scan is obtained before the second 3D scan.

30. The method according to any one or more of the preceding embodiments, wherein the second 3D scan is obtained before the first 3D scan.

31. The method according to any one or more of the preceding embodiments, wherein the first 3D scan or the second 3D scan comprises the damaged tooth, the outer part of the scan pin, if the scan pin is inserted in the tooth, and at least one or more neighbor teeth or the neighborhood, if no teeth as neighbors.

32. The method according to any one or more of the preceding embodiments, wherein the second 3D scan or the first 3D scan comprises only at least part of the damaged tooth, and the outer part of the scan pin, if the scan pin is inserted in the tooth.

33. The method according to any one or more of the preceding embodiments, wherein the 3D scan obtained first comprises the damaged tooth, the outer part of the scan pin, if the scan pin is inserted in the tooth, and at least one or more neighbor teeth.

34. The method according to any one or more of the preceding embodiments, wherein the 3D scan obtained secondly comprises only the damaged tooth, and the outer part, if the scan pin is inserted in the tooth.

35. The method according to any one or more of the preceding embodiments, wherein virtually designing the post and core comprises providing a cement gap relative to the post part and/or relative to the core part.

36. The method according to any one or more of the preceding embodiments, wherein virtually designing the post and core comprises providing a tapering angle of the core.

37. The method according to any one or more of the preceding embodiments, wherein virtually designing the post and core comprises providing an anatomic top of the core for fitting to the anatomy of the crown.

38. The method according to any one or more of the preceding embodiments, wherein virtually designing the post and core comprises providing an anatomic top of a coping for fitting to the anatomy of the crown.

39. The method according to any one or more of the preceding embodiments, wherein virtually designing the post and core comprises defining a distance from the core to the top of the crown.

40. The method according to any one or more of the preceding embodiments, wherein virtually designing the post and core comprises automatically generating the core.

41. The method according to any one or more of the preceding embodiments, wherein designing a crown for the post and core comprises blocking out areas identified as undercuts.

42. The method according to any one or more of the preceding embodiments, wherein designing a crown for the post and core comprises offsetting the shape of the core.

43. The method according to any one or more of the preceding embodiments, wherein designing the core comprises offsetting the crown.

44. The method according to any one or more of the preceding embodiments, wherein designing a crown for the post and core comprises providing margins lines for the core and/or for a coping and/or for the crown.

45. The method according to any one or more of the preceding embodiments, wherein virtually designing the post and core comprises designing the crown before designing the post and core.

46. The method according to any one or more of the preceding embodiments, wherein virtually designing the post and core comprises designing the post and core before designing the crown.

47. The method according to any one or more of the preceding embodiments, wherein virtually designing the post and core comprises designing a coping between designing the crown and the post and core.

48. The method according to any one or more of the preceding embodiments, wherein virtually designing the post and core comprises:
designing the crown first,
designing the post and core secondly, and
designing the coping finally.

49. The method according to any one or more of the preceding embodiments, wherein the post part or inner part of the scan pin and the drill which drilled the bore in the tooth have similar shapes.

50. The method according to any one or more of the preceding embodiments, wherein the post is designed to have a shape similar to the post part of the scan pin and/or to the drill which drilled the bore in the tooth.

51. The method according to any one or more of the preceding embodiments, wherein obtaining a 3D scan of at least part of the patient's set of teeth comprises performing a 3D scanning intra orally of the patient using an intra oral scanner.

52. The method according to any one or more of the preceding embodiments, wherein obtaining a 3D scan of at least part of the patient's set of teeth comprises performing a 3D scanning of a physical model of the patient's teeth in a desktop scanner or using an intra oral scanner.

53. The method according to any one or more of the preceding embodiments, wherein obtaining a 3D scan of at least part of the patient's set of teeth comprises performing a 3D scanning of a physical impression of the patient's teeth in a desktop scanner or using an intra oral scanner.

54. The method according to any one or more of the preceding embodiments, wherein the 3D scan is a surface scan.

55. The method according to any one or more of the preceding embodiments, wherein the 3D scan is a CT scan.

56. The method according to any one or more of the preceding embodiments, wherein the 3D scan is performed by means of laser light scanning, white light scanning, probe-scanning, X-ray scanning, and/or CT scanning.

57. A computer program product comprising program code means for causing a data processing system to perform the method according to any one or more of the preceding claims, when said program code means are executed on the data processing system.

58. A computer program product, comprising a computer-readable medium having stored there on program code means according to the preceding claim.

59. A non-transitory computer readable medium storing thereon a computer program, where said computer program is configured for causing a computer-assisted method of virtually designing a post and core restoration adapted for attachment in a damaged tooth of a patient, where the damaged tooth comprises a bore for receiving the post of the post and core, wherein the method comprises:
    obtaining a 3D image comprising a first 3D scan comprising at least a part of the damaged tooth;
    providing a digital 3D shape of at least a part of a component adapted for fitting to the damaged tooth, where the component comprises at least a post part adapted for fitting in the bore of the damaged tooth;
    virtually matching the first 3D scan of the tooth and the digital 3D shape of the component, where the matching comprises matching a surface region in the first 3D scan of the tooth with a corresponding surface region of the digital 3D shape component, such that at least part of the post part of the digital 3D shape of the component is represented relative to the first 3D scan of the tooth;
    virtually designing the post and core restoration based on the representation of the post part of the digital 3D shape of the component relative to the first 3D scan of the tooth.

60. A system for virtually designing a post and core restoration adapted for attachment in a damaged tooth of a patient, where the damaged tooth comprises a bore for receiving the post of the post and core, wherein the system comprises:
    means for obtaining a 3D image comprising a first 3D scan comprising at least a part of the damaged tooth;
    means for providing a digital 3D shape of at least a part of a component adapted for fitting to the damaged tooth, where the component comprises at least a post part adapted for fitting in the bore of the damaged tooth;
    means for virtually matching the first 3D scan of the tooth and the digital 3D shape of the component, where the matching comprises matching a surface region in the first 3D scan of the tooth with a corresponding surface region of the digital 3D shape component, such that at least part of the post part of the digital 3D shape of the component is represented relative to the first 3D scan of the tooth;
    means for virtually designing the post and core restoration based on the representation of the post part of the digital 3D shape of the component relative to the first 3D scan of the tooth.

61. The system according to the preceding embodiment, wherein the system comprises a nontransitory computer readable medium having one or more computer instructions stored thereon, where said computer instructions comprises instructions for carrying out a method of virtually designing a post and core restoration adapted for attachment in a damaged tooth of a patient, where the damaged tooth comprises a bore for receiving the post of the post and core, wherein the method comprises:
    obtaining a 3D image comprising a first 3D scan comprising at least a part of the damaged tooth;
    providing a digital 3D shape of at least a part of a component adapted for fitting to the damaged tooth, where the component comprises at least a post part adapted for fitting in the bore of the damaged tooth;
    virtually matching the first 3D scan of the tooth and the digital 3D shape of the component, where the matching comprises matching a surface region in the first 3D scan of the tooth with a corresponding surface region of the digital 3D shape component, such that at least part of the post part of the digital 3D shape of the component is represented relative to the first 3D scan of the tooth;
    virtually designing the post and core restoration based on the representation of the post part of the digital 3D shape of the component relative to the first 3D scan of the tooth.

62. A scan pin for determining the position, depth and/or orientation of a bore drilled in a damaged tooth, the scan pin comprises a scan head and a scan post extending from the scan head wherein the shape of the scan post in at least one area corresponds to the shape of at least a part of the working surface shape of a drill used to drill the bore.

63. A scan pin according to embodiment 62, wherein the scan post has a tapering diameter.

64. A scan pin according to embodiment 62 or 63, wherein the scan has no through going bores.

The invention claimed is:
1. A method of virtually designing a post and core restoration adapted for attachment in a damaged tooth of a patient, where the damaged tooth includes a bore for receiving the post of the post and core, wherein the method comprises:
    obtaining a 3D image on a computer, wherein the 3D image comprises a first 3D scan of at least a part of the damaged tooth, where a scan pin comprising an outer part and an inner part is arranged in the bore of the damaged tooth during the imaging of the first 3D scan, such that the outer part of the scan pin is located at least partly outside the bore of the tooth, and the inner part of the scan pin is located at least partly in the bore of the tooth, where the inner part of the scan pin corresponds to the post of the post and core, and where the first 3D scan comprises at least a part of the tooth and the scan pin;
    providing a digital 3D shape of the scan pin on a computer, wherein the digital 3D shape of the scan pin includes the outer part and the inner part of the scan pin;
    matching the first 3D scan with the digital 3D shape of the scan pin using a computer, where the matching comprises matching the at least part of the scan pin of the first

3D scan with the at least part of the scan pin of the digital 3D shape, such that the inner part of the scan pin of the digital 3D shape is represented relative to the tooth of the first 3D scan; and designing the post and core restoration on a computer, where the designing is based on the representation of the inner part of the scan pin relative to the tooth in the first 3D scan.

2. A method according to claim 1, further comprising that the digital 3D shape is at least a part of a surface representation adapted for matching at least a part of the bore of the damaged tooth.

3. The method according to claim 1, wherein the matching and the designing are done virtually.

4. The method according to claim 3, wherein the method further comprises: virtually deleting the outer part of the scan pin from the first 3D scan after the matching.

5. The method according to claim 4, wherein virtually deleting the outer part of the scan pin from the first 3D scan comprises deleting points in an area surrounding the shape of the outer part of the digital 3D shape.

6. The method according to claim 4, wherein the method further comprises:

performing virtual hole closing of the missing surface which arise after deletion of the outer part of the scan pin from the first 3D scan.

7. The method according to claim 4, wherein the method further comprises: offsetting the surface of the 3D scan and/or the surface of the 3D digital shape to obtain a closed surface after deletion of the outer part of the scan pin.

8. The method according to claim 3, wherein the matching comprises overlaying the first 3D scan of the tooth and the digital 3D shape of the scan pin.

9. The method according to claim 1, further comprising virtually providing the inner part of the scan pin from the 3D digital shape to the first 3D scan.

10. The method according to claim 1, wherein the 3D image further comprises a second 3D scan of at least part of the patient's set of teeth comprising the damaged tooth, where no scan pin is arranged in the tooth bore during the 3D scanning, and where the second 3D scan comprises at least part of a cavity of the tooth adapted for attachment of the post and core in the tooth.

11. The method according to claim 10, wherein the 3D image is a virtual combination of the first 3D scan comprising the tooth and the component with the second 3D scan only comprising the tooth.

12. The method according to claim 1, wherein the post and core restoration adapted for attachment in a damaged tooth comprises at least two posts, whereby the damaged tooth comprises at least two bores, and where a first post of the at least two posts is adapted for attachment in a first bore of the at least two bores, and where a second post of the at least two posts is adapted to attachment in a second bore of the at least two bores.

13. The method according to claim 1, wherein designing a crown for the post and core comprises providing margin lines for the core and/or for a coping and/or for the crown.

14. The method according to claim 1, wherein the post part or inner part of the scan pin and a drill which drilled the bore in the tooth have similar shapes.

15. The method according to claim 1, wherein the post is designed to have a shape similar to the post part of the scan pin and/or to a drill which drilled the bore in the tooth.

16. The method according to claim 1, wherein the matching includes matching a surface region in the first 3D scan of the tooth with a corresponding surface region of the digital 3D shape such that at least part of the post of the digital 3D shape is represented relative to the first 3D scan of the tooth.

* * * * *